United States Patent [19]

Yamada et al.

[11] Patent Number: 4,594,099
[45] Date of Patent: Jun. 10, 1986

[54] N-SUBSTITUTED-$\Delta^1$-TETRAHYDROPHTHALIMIDE DERIVATIVES

[75] Inventors: Osamu Yamada, Ageo; Mikio Yanagi, Okegawa; Fumio Futatsuya, Ohmiya; Kenji Kobayashi, Okegawa, all of Japan

[73] Assignee: Nippon Kayaku Kabushiki Kaisha, Tokyo, Japan

[21] Appl. No.: 540,691

[22] Filed: Oct. 11, 1983

Related U.S. Application Data

[63] Continuation of Ser. No. 241,021, Mar. 6, 1982, abandoned.

[30] Foreign Application Priority Data

Mar. 12, 1980 [JP] Japan ................................. 55-30267
Dec. 24, 1980 [JP] Japan ................................ 55-181850

[51] Int. Cl.$^4$ .................... A01N 43/38; C07D 209/48
[52] U.S. Cl. ........................................ 71/96; 548/513
[58] Field of Search ...................... 71/96; 260/326 A; 548/513

[56] References Cited

U.S. PATENT DOCUMENTS 3,878,224   4/1975   Matsui et al. ..................... 260/326
3,984,435  10/1976   Matsui et al. ................... 260/326 A
4,292,070   9/1981   Wakabayashi et al. ............... 71/96

FOREIGN PATENT DOCUMENTS 55-139359 10/1979 Japan .

OTHER PUBLICATIONS

Acta Pol. Pharm. 1976, 33(1), 115-23 (Pol).

Primary Examiner—Catherine L. Mills
Attorney, Agent, or Firm—Wegner & Bretschneider

[57] ABSTRACT

New herbicidal N-substituted-$\Delta^1$-tetrahydrophthalimide derivatives represented by the formula:

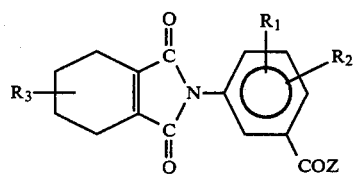

28 Claims, No Drawings

N-SUBSTITUTED-Δ¹-TETRAHYDROPHTHALIMIDE DERIVATIVES

This application is a continuation of U.S. application Ser. No. 241,021, filed Mar. 6, 1982, abandoned.

DETAILED DESCRIPTION OF THE INVENTION

The present invention relates to new N-substituted-Δ¹-tetrahydrophthalimide derivatives represented by the formula:

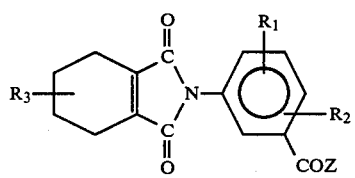

wherein $R_1$ is hydrogen, halogen, lower alkyl, lower alkoxy or nitro, $R_2$ is hydrogen, lower alkyl or halogen, $R_3$ is hydrogen or lower alkyl and Z is hydroxy or metal salt thereof, chain alkoxy that may have halogen, lower alkoxy, lower alkoxyalkoxy or cyano as substitution groups alicyclic alkoxy, alkenyloxy or alkynyloxy, phenoxy that may have halogen, lower alkyl or lower alkoxy as substitution groups, aralkyloxy that may have halogen, lower alkyl or lower alkoxy as substitution group, alkylthio or amino, primary or secondary alkylamino that may have halogen and hydroxy as substitution groups, alkenylamino that may have halogen as substitution group or morpholino that may have lower alkyl as substitution groups or metal salt of hydroxy (Z is not hydroxy when $R_1$, $R_2$ and $R_3$ are hydrogen), and preparation methods thereof, a herbicidal composition comprising one or more of said derivatives as active ingredients and further to a method of killing weeds using said compounds.

It is known that N-substituted-Δ¹-tetrahydrophthalimide derivatives have herbicidal activity. The present inventors found the fact that a compound formed by introducing carboxy or its derivative into meta position of a N-substituted phenyl derivative shows remarkably strong herbicidal activity as compared with known compounds and have completed the present invention.

As N-substituted phenyl derivatives having carboxy, there can be mentioned known compound No.1 which has carboxy in para position as shown in Agr. Biol. Chem., 40(4), 749-751, 1976, but the compound No.1 is much inferior to the known compound No.2 (MK-616) in herbicidal activity. Therefore the introduction of carboxy has been considered undesirable for fear of lowering herbicidal activity.

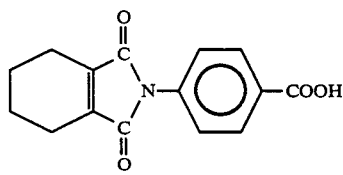
(known compound No. 1)

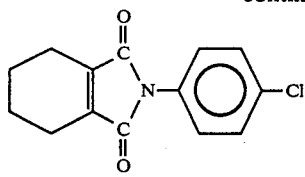
(known compound No. 2)

However, a compound of the formula (I) wherein carboxy or its derivative group is introduced into the meta position has unexpectedly strong herbicidal activity. In the paddy field it exhibits excellent herbicidal effect in a low dosage not only against annual weeds such as barnyerd grasses and broadleaf weeds, but also has a strong effect on perennial weeds such as mizugayatsuri, bulrush, water chestnut, needle spikerush and arrowhead. In a up-land too, the compound shows a good herbicidal effect by both pre- and post-emergence treatments and it has been found to be extremely effective in a low dosage especially against such broadleaf weeds as those of amaranth, goosefoot and buckweat families. On the other hand, the compound is hardly phytotoxic to crops such as rice, wheat, oat, corn, soybean, cotton, sunflower, etc. and it has proved to be a herbicidal composition of practical use.

As halogen in the compound of formula (I) of the present invention, there can be mentioned chlorine, bromine or fluorine. Lower alkyls include alkyl having 1 to 4 carbon atoms such as methyl, ethyl, propyl and butyl, and lower alkoxy includes alkoxy having 1 to 4 carbon atoms such as methoxy, ethoxy, n-propoxy, isopropoxy, n-butoxy and sec-butoxy. As examples of chain alkoxy there can be mentioned chain alkoxy having 1 to 8 carbon atoms such as methoxy, ethoxy, n-propoxy, isopropoxy, n-butoxy, sec-butoxy, isobutoxy, tert-butoxy, n-pentyloxy, isopentyloxy, 1,1-dimethylpropoxy, n-hexyloxy, 1-methylpentyloxy, 1,3-dimethylbutoxy, 1-ethylbutoxy, n-heptyloxy, 1-ethylpentyloxy, n-octyloxy, 1-ethylhexyloxy and 2,2-dimethyl-4-methylpentyloxy.

As examples of chain alkoxy that may have halogen, lower alkoxy lower alkoxyalkoxy or cyano as substitution groups, there can be mentioned substituted chain alkoxy having 2 to 8 carbon atoms such as 2-chloroethoxy, 2,2,2-trichloroethoxy, 2-chloro-1-chloromethylethoxy, 6-chloro-n-hexyloxy, 1-chloromethylethoxy, 2-methoxyethoxy, 2-ethoxyethoxy, 2-methoxy-1-methylethoxy, 2-butoxyethoxy, 2-isopropoxyethoxy and 2-(2'-methoxyethoxy)ethoxy, α-cyano-ethoxy, β-cyano-ethoxy, α-cyano-propoxy, α-cyano-heptyloxy, α-cyano-octyloxy or

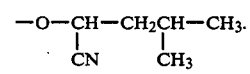

As alicyclic alkoxy there can be mentioned those having 3 to 7 carbon atoms such as cyclopropoxy, cyclobutoxy, cyclopentyloxy, cyclohexyloxy and cycloheptyloxy.

As alkenyloxy there can be mentioned those having 2 to 5 carbon atoms such as allyloxy, 2-buthenyloxy, 1-methylallyloxy and 2-pentenyloxy, and alkynyloxys include those having 3 to 4 carbon atoms such as propargyloxy, 2-butynyloxy, 3-butynyloxy and 1-methylpropargyloxy.

As examples of phenoxy that may have halogen, lower alkyl or lower alkoxy as substitution group there can be mentioned phenoxy, o-, m- or p-chlorophenoxy, o-, m- or p-methylphenoxy and o-, m- or p-methoxyphenoxy.

As examples of aralkyloxy that may have halogen, lower alkyl or lower alkoxy as substitution group there can be mentioned benzyloxy, phenethyloxy, chlorobenzyloxy, methylbenzyloxy and methoxybenzyloxy.

As examples of alkylthio having 1 to 8 carbon atoms, there can be mentioned methylthio, ethylthio, n-propylthio, isopropylthio, sec-butylthio, n-amylthio, isoamylthio, tertamylthio and n-octylthio.

As primary or secondary alkylamino that may have halogen and hydroxy as substitution group there can be mentioned, those having 1 to 8 carbon atoms such as methylamino, ethylamino, propylamino, isopropylamino, isobutylamino, isoamylamino, n-hexylamino, n-octylamino, dimethylamino, diethylamino, dipropylamino, diisobutylamino, methylethylamino, ethylbutylamino, propylbutylamino and 1-hydroxy-2,2,2-trichloroethylamino.

As alkenylamino that may have halogen as substitution groups there can be mentioned those having 3 to 5 carbon atoms such as allylamino, allylmethylamino and β,β-dichlorovinylamino.

As examples of morpholino that may have lower alkyl as substitution groups are morpholino, 2-methylmorpholino and 2,6-dimethylmorpholino.

As examples of metal salt of hydroxy there can be mentioned those of alkaline metals such as sodium and potassium, alkaline earth metals such as calcium and manganese.

The new N-substituted-Δ¹-tetrahydrophthalimide derivative represented by the formula (I) can be prepared by the processes described in (a), (b) and (c) below.

(a) When Z is one of those described above excluding metal salt of hydroxy, the compound of the formula (I) can be obtained by the following methods (1) to (4).

(1) Δ¹-tetrahydrophthalic anhydride represented by the formula (II) below (wherein $R_3$ is hydrogen or lower alkyl) is reacted under heating with a compound represented by the formula (III) below (wherein $R_1$ is hydrogen, halogen, lower alkyl, lower alkoxy or nitro, $R_2$ is hydrogen, halogen or lower alkyl and Z is as defined above) without or in the presence of a suitable solvent to obtain a compound of the formula (I).

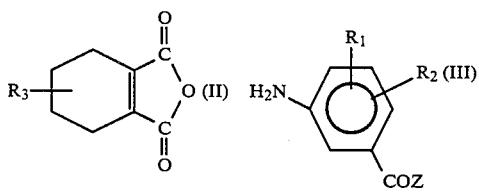

(2) When said reaction is carried out under an easy condition, a compound represented by the formula (VI):

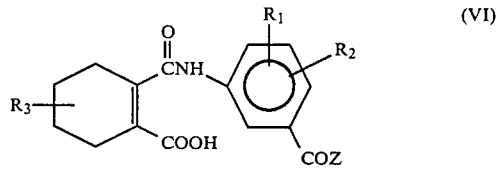

(wherein $R_1$, $R_2$, $R_3$ and Z are the same as defined in the formulas (II) and (III) above) is obtained as an intermediate. The compound is cyclized under heating to obtain a compound of the formula (I).

(3) The compound of the formula (VI) is esterified according to the usual method and a resulting compound represented by the formula (VII):

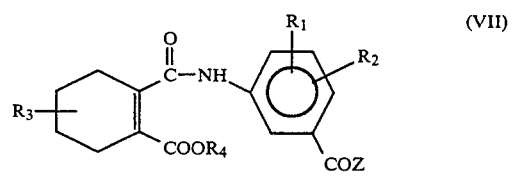

(wherein $R_1$, $R_2$, $R_3$ and Z are the same as defined in the formula (VI), and $R_4$ is lower alkyl such as methyl, ethyl, propyl or butyl) is cyclized under heating to obtain a compound of the formula (I).

Any of these reactions can be carried out without a solvent occasionally, but it is generally better to use a solvent. The reaction is continued for 30 minutes to 5 hours at a temperature 50° to 200° C., preferably 80° to 150° C.

As solvents there can be used lower fatty acids such as acetic acid and propionic acid, aromatic compounds such as toluene, xylene and chlorobenzene, hydrocarbon halides such as chloroform, carbon tetrachloride and perclene, alcohols such as methanol and ethanol, ketones such as acetone and methylethylketone, and dioxane, tetrahydrofurane, water, etc. as well. And these reaction may also be conducted in the presence o acid catalysts (for example p-toluenesulfonic acid, sulfuric acid, hydrogen chloride, etc.), salts (for example sodium acetate, potassium acetate, etc.), phosphor oxychloride and others. and further (4) Starting with a compound represented by the formula (IV):

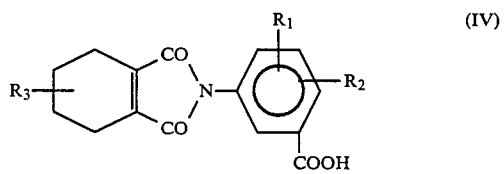

(wherein $R_1$, $R_2$ and $R_3$ are as defined in the formula (I)) which is obtained by said reaction (a compound of the formula (I) wherein Z is hydroxy and also obtainable by hydrolysis of esters of the formula (I)), it is esterified with a compound represented by the formula:

Z—H        (III)'

(wherein Z is as defined above) in the presence of an acid catalyst (same as above) to obtain a compound of the formula (I).

(b) When Z is a metal salt of hydroxyl group, a compound of the formula (I) is reacted in a usual way with alkaline metals such as sodium hydroxide and potassium hydroxide, alkaline earth metals such as calcium hydroxide and calcium chloride, manganese salts such as manganese chloride or others to obtain a compound of the formula (I).

By the way the metal salt of hydroxyl group can be represented by the following formulas: in case of monovalent metal atom

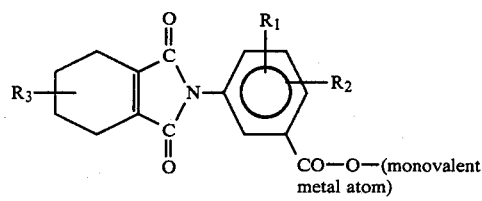

(wherein $R_1$, $R_2$ and $R_3$ are as defined above) and in case of bivalent metal atom

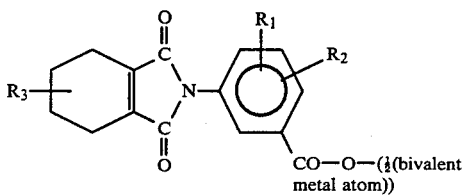

(c) When Z is chain alkoxy that may have halogen, lower alokoxy, lower alkoxyalkoxy or cyano as substitution groups, alicyclic alkoxy, alkenyloxy or alkynyloxy, phenoxy that may have halogen, lower alkyl or lower alkoxy as substitution groups, aralkyloxy that may have halogen, lower alkyl or lower alkoxy as substitution groups, alkylthio or amino, primary or secondary alkylamino that may have halogen and hydroxy as substitution groups, alkenylamino that may have halohgen as substitution groups or morpholino that may have lower alkyl as substitution groups, a compound of the formula (IV) is reacted with a chlorinating agent such as thionyl chloride or phosphor oxychloride to produce a compound represented by the formula (V):

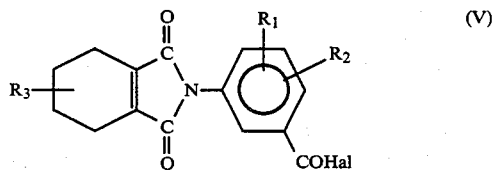 (V)

(wherein $R_1$, $R_2$ and $R_3$ are as defined in the formula (I) and Hal is chloro or bromo). The resulting compound is then reacted with alcohols, alkyl mercaptans, amines, ammonia or solution thereof, phenols or morpholinos, represented by the formula:

$$Z—H \quad \quad (III)'$$

(wherein Z is as defined in (c) above) if necessary in the presence of a suitable base, to obtain a compound of the formula (I).

As used in the above reaction, alcohols include compounds wherein hydrogen combines respectively with said chain alkoxy, said alicyclic alkoxy, said chain alkoxy that may have halogen or lower alkoxy as substitution groups, said alkenyloxy, said alkynyloxy and said aralkyloxy that may have halogen, lower alkyl or lower alkoxy as substitution groups, and alkylmercaptans include compounds wherein hydrogen combines with said alkylthio. And examples of amines are compounds wherein hydrogen combines respectively with said primary or secondary alkylamino that may have halogen and hydroxy as substitution groups and alkenylamino that may have halogen as substitution groups, and examples of phenols and morpholinos are compounds wherein hydrogen combines respectively with said phenoxy that may have halogen, lower alkyl or lower alkoxy and said morpholino that may have lower alkyl correspondingly as substitution groups.

As compounds of the present invention which show preferable herbicidal effect, there can be mentioned those of the formula (I) wherein $R_1$ is halogen or lower alkyl, $R_2$ is hydrogen, lower alkyl or halogen, $R_3$ is hydrogen or lower alkyl and Z is hydroxy, chain alkoxy having 1 to 8 carbon atoms that may have halogen, lower alkoxy, lower alkoxyalkoxy or cyano as substitution groups, alicyclic alkoxy having 3 to 7 carbon atoms, alkenyloxy having 2 to 5 carbon atoms, alkylthio having 1 to 8 carbon atoms, primary or secondary alkylamino having 1 to 8 carbon atoms that may have halogen or hydroxy as substitution groups or alkenylamino having 3 to 5 carbon atoms that may have halogen as substitution groups, or metal salt of hydroxyl.

More preferred compounds of the present invention are those of the formula (I) wherein $R_1$ is halogen or lower alkyl, $R_2$ is hydrogen, lower alkyl or halogen, $R_3$ is hydrogen or lower alkyl and Z is chain alkoxy having 1 to 8 carbon atoms that may have lower alkoxy or cyano as substitution group, primary alkylamino having 1 to 8 carbon atoms that may have halogen and hydroxy as substitution groups, metal salt of hydroxy or hydroxy.

Moreover the compounds which exhibit most preferable herbicidal effect are those of the formula (I) wherein $R_1$ is Cl or Br, $R_2$ is hydrogen, Cl or F, $R_3$ is hydrogen or methyl and Z is chain alkyloxy having 2 to 4 carbon atoms. Examples of such compound include those which are given in the table below as compounds Nos. 3,5,7,8,10,27,29,30,63,64,65,85,86, 88,89,92,103,104,114,130,133 and 148.

The detailed explanation will be given in the following examples.

Synthesis Example 1:
N-(4,6-dichloro-3-carboxyphenyl)-$\Delta^1$-tetrahydrophthalimide (No. 1)

160 ml of acetic acid were added to a mixture of 18.4 g (0.121 mol) of $\Delta^1$-tetrahydrophthalic anhydride and 25 g (0.121 mol) of 2,4-dichloro-5-aminobenzoic acid, the solution was heated under reflux for 5 hours and then poured into ice water. The obtained crystals were filtered, washed with water and recrystallized from ethanol to obtain 36.3 g (yield: 88%) of light brown crystals. Melting point: 247°–249° C.

Elementary analysis: $C_{15}H_{11}Cl_2NO_4$; Calculated: C: 52.96, H: 3.26, N: 4.12; Found: C: 52.71, H: 3.10, N: 4.03.

Synthesis Example 2:
N-(4,6-dichloro-3-methoxycarbonylphenyl)-Δ¹-tetrahydropathalimide (No. 2)

6.4 g (0.2 mol) of methanol, 1 g (0.005 mol) of p-toluenesulfonic acid and 50 ml of toluene were added to 3.4 g (0.01 mol) of above obtained N-(4,6-dichloro-3-carboxyphenyl)-Δ¹-tetrahydrophthalimide, the mixture was heated under reflux for 10 hours, cooled down and washed with saturated aqueous solution of sodium bicarbonate. Then the solution was washed with water to become neutral, dried with sodium sulfate anhydride and concentrated to produce crystals, which were recrystallized from methanol to obtain 3.1 g (yield: 87%) of white crystals. Melting point: 102°–103° C.

Elementary analysis: $C_{16}H_{13}Cl_2NO_4$; Calculated: C: 54.26, H: 3.70, N: 3.95; Found: C: 54.35, H: 3.51, N: 3.74.

Synthesis Example 3:
N-(4,6-dichloro-3-ethoxycarbonylphenyl)-Δ¹-tetrahydrophthalimide (No. 3)

9.2 g (0.2 mol) of ethanol, 50 ml of toluene and a small amount of concentrated sulfuric acid were added to 3.4 g (0.01 mol) of N-(4,6-dichloro-3-carboxyphenyl)-Δ¹-tetrahydrophthalimide, heated under reflux for 10 hours, cooled down, washed with saturated aqueous solution of sodium bicarbonate and further washed with water. Then the solution was dried with sodium sulfate anhydride, concentrated and the resulting crystals were recrystallized from methanol to obtain 3.0 g (yield: 81%) of white crystals. Melting point: 115°–117° C.

Elementary analysis: $C_{17}H_{15}Cl_2NO_4$; Calculated: C: 55.45, H: 4.11, N: 3.80; Found: C: 55.64, H: 4.02, N: 3.61.

Synthesis Example 4:
N-(4,6-dichloro-3-isopropoxycarbonylphenyl)-Δ¹-tetrahydrophthalimide (No. 5)

50 ml of acetic acid were added to a mixture of 3.04 g (0.02 mol) of Δ¹-tetrahydrophthalic anhydride and 4.96 g (0.02 mol) of isopropyl 5-amino-2,4-dichlorobenzoate, heated under reflux for 5 hours and then poured into ice water. The obtained crystals were filtered, washed with water and recrystallized from ethanol to obtain 6.6 g (yield: 86%) of white crystals. Melting point: 109°–110° C.

Elementary analysis: $C_{18}H_{17}Cl_2NO_4$; Calculated: C: 56.56, H: 4.48, N: 3.66; Found: C: 56.51, H: 4.44, N: 3.51.

Synthesis Example 5:
N-(3-ethoxycarbonyl-4-chloro-6-fluorophenyl)-Δ¹-tetrahydrophthalimide (No. 63)

70 ml of acetic acid were added to a mixture of 2.80 g (0.018 mol) of Δ¹-tetrahydrophthalic anhydride and 3.93 (0.018 mol) of ethyl 5-amino-2-chloro-4-fluorobenzoate, heated under reflux for 5 hours and then poured into ice water. The obtained crystals were filtered, washed with water, dried and recrystallized from a mixed solution of benzene and n-hexane to obtain 4.9 g (yield: 78%) of orange-colored crystals. Melting point: 92°–95° C.

Elementary analysis: $C_{17}H_{15}ClFNO_4$; Calculated: C: 58.05, H: 4.30, N: 3.98; Found: C: 57.86, H: 4.13, N: 3.85.

Synthesis Example 6:
N-(3-n-propoxycarbonyl-4,6-dichlorophenyl-Δ¹-tetrahydrophthalimide (No. 4)

1.1 g (0.018 mol) of n-propanol and 20 ml of toluene were added to 3.23 g (0.009 mol) of N-(3-chlorocarbonyl-4,6-dichlorophenyl)-Δ¹-tetrahydrophthalimide. 1.1 g (0.011 mol) of triethylamine were added dropwise into the mixture while stirring and the reaction was carried out for one hour at room temperature. Then the mixture was washed with saturated aqueous solution of sodium bicarbonate and further with water, dried with sodium sulfate anhydride and concentrated to produce 3.1 g (yield: 90%) of white crystals. The crystals were recrystallized from mixed solution of benzene and n-hexane to obtain 2.5 g (yield: 73%) of white crystals. Melting point: 123.5°–125.5° C.

Elementary analysis: $C_{18}H_{17}Cl_2NO_4$; Calculated: C: 56.56, H: 4.48, N: 3.66; Found: C: 56.47, H: 4.33, N: 3.38.

The above compound can also be obtained by conducting a similar reaction to the above using N-(3-bromocarbonyl-4,6-dichlorophenyl)-Δ¹-tetrahydrophthalimide instead of N-(3-chlorocarbonyl-4,6-dichlorophenyl)-Δ¹-tetrahydrophthalimide.

Synthesis Example 7:
N-(3-ethylthiocarbonyl-4,6-dichlorophenyl)-Δ¹-tetrahydrophthalimide (No. 23)

30 ml of toluene were added to 2.15 g (0.006 mol) of N-(3-chlorocarbonyl-4,6-dichlorophenyl)-Δ¹-tetrahydrophthalimide, cooled down below 10° C. while stirring, 0.5 g (0.008 mol) of ethyl mercaptan was added and 0.62 g (0.006 mol) of triethylamine was dropped slowly. After stirring for one hour, the mixture was washed with water, dried with sodium sulfate anhydride, concentrated to produce crystals and the resulting crystals were recrystallized from mixed solution of toluene and n-hexane to obtain 1.9 g (yield: 82%) of white crystals. Melting point: 74°–78° C.

Elementary analysis: $C_{17}H_{15}Cl_2NO_3S$; Calculated: C: 53.13, H: 3.93, N: 3.64; Found: C: 52.78, H: 3.59, N: 3.46.

Synthesis Example 8:
N-(3-N'-ethylcarbamoyl-4,6-dichlorophenyl)-Δ¹-tetrahydrophthalimide (No. 77)

30 ml of toluene were added to 3.59 g (0.010 mol) of N-(3-chlorocarbonyl-4,6-dichlorophenyl)-Δ¹-tetrahydrophthalimide, cooled down below 10° C. while stirring and 1.35 g (0.021 mol) of 70% aqueous solution of ethyl amine were dropped slowly. After dropping, the cooling bath was removed and the mixture was stirred for one hour at room temperature, washed with water, dried with sodium sulfate anhydride, concentrated and the resulting crystals were recrystallized from mixed solution of toluene and n-hexane to obtain 3.0 g (yield: 82%) of light yellow crystals. Melting point: 89°–94° C.

Elementary analysis: $C_{17}H_{16}Cl_2N_2O_3$; Calculated: C: 55.60, H: 4.39, N: 7.63; Found: C: 55.22, H: 4.75, N: 7.99.

Synthesis Example 9:
4,6-dichloro-3-(Δ¹-tetrahydrophthalimide-1-il)sodium benzoate (No. 69)

250 ml of ethyl alcohol were added to 15.64 g (0.046 mol) of 4,6-dichloro-3-(3,4,5,6-tetrahydrophthalimide-1-il)benzoic acid, 100 ml of ethyl alcohol wherein 3.36 g (purity: 92.5%, 0.046 mol) of sodium ethoxide were dissolved, were added slowly to the mixture to form a uniform layer, concentrated under reduced pressure and the resulting crystals were washed with toluene to obtain 15.5 g (yield: 93%) of yellowish crystals. Melting point: more than 270° C.

Elementary analysis: $C_{15}H_{10}Cl_2NO_4Na$; Calculated: C: 49.75, H: 2.78, N: 3.87; Found: C: 49.43, H: 2.51, N: 3.54.

Synthesis Example 10:
N-(3-i-propoxycarbonyl-4-chlorophenyl)-Δ¹-tetrahydrophthalimide (No. 149)

50 ml of acetic acid were added to 16.5 g (0.05 mol) of 2-[(3-i-propoxycarbonyl-4-chlorophenyl)carbamoyl]-1-cyclohexene-1-carbonic acid, heated under reflux for 4 hours and then poured into ice water. The obtained crystals were filtered, washed with water, dried and recrystallized from mixed solution of benzene and n-hexane to obtain 15.6 g (yield: 90%) of white crystals. Melting point: 85°–85.5° C.

Synthesis Example 11:
N-(3-methoxycarbonyl-4-chlorophenyl)-Δ¹-tetrahydrophthalimide (No. 146)

30 ml of acetic acid were added to 6.3 g (0.02 mol) of methyl 2-[(3-methoxycarbonyl-4-chlorophenyl)carbamoyl]-1-cyclohexene-1-carboxylate, heated under reflux for 5 hours and then poured into ice water. The obtained crystals were filtered, washed with water, dried and recrystallized from mixed solution of benzene and n-hexane to obtain 5.9 g (yield: 93%) of white crystals. Melting point: 123°–123.5° C.

Examples of those compounds obtained by the above-mentioned methods are given in Table 1 below.

TABLE 1

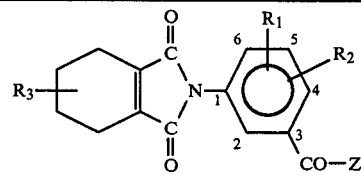

| No. | $R_1$ | $R_2$ | $R_3$ | Z | m.p. (°C.) or refractive index |
|---|---|---|---|---|---|
| 1 | 4-Cl | 6-Cl | H | OH | 247–9 |
| 2 | " | " | " | $OCH_3$ | 102–3 |
| 3 | " | " | " | $OC_2H_5$ | 115–7 |
| 4 | " | " | " | $OC_3H_7(n)$ | 123.5–5.5 |
| 5 | " | " | " | $OC_3H_7(i)$ | 109–110 |
| 6 | " | " | " | $OC_4H_9(n)$ | 92.5–4 |
| 7 | " | " | " | $OC_4H_9(sec)$ | $n_D^{25}1.5650$ |
| 8 | 4-Br | 6-F | " | $OC_3H_7(i)$ | $n_D^{25}1.5565$ |
| 9 | 4-Cl | 6-Cl | " | O—⬠ | (amorphous) ($n_D^{25}1.5600$) |
| 10 | " | " | " | $OC_5H_{11}(sec)$ | $n_D^{25}1.5580$ |
| 11 | " | " | " | $OCH(CH_3)CH(CH_3)CH_3$ | $n_D^{25}1.5607$ |
| 12 | " | " | " | $OC_6H_{13}(n)$ | $n_D^{25}1.5555$ |
| 13 | " | " | " | $OCH(CH_3)(CH_2)_3CH_3$ | $n_D^{25}1.5542$ |
| 14 | " | " | " | $OCH(CH_3)CH_2CH(CH_3)CH_3$ | $n_D^{25}1.5538$ |
| 15 | " | " | " | $OCH(CH_3)(CH_2)_5CH_3$ | $n_D^{25}1.5472$ |
| 16 | " | " | " | $OCH(C_2H_5)(CH_2)_4CH_3$ | $n_D^{25}1.5450$ |
| 17 | " | " | " | $OCH_2C(CH_3)_2CH_2CH(CH_3)CH_3$ | $n_D^{25}1.5496$ |
| 18 | " | " | " | $OCH_2CH{=}CH_2$ | 116–8.5 |
| 19 | " | " | " | $OCH_2C{\equiv}CH$ | 132.5–5 |
| 20 | " | " | " | $OCH_2CH_2Cl$ | 91–2.5 |
| 21 | " | " | " | $OCH_2{-}\text{Ph}$ | 93–6 |
| 22 | " | " | " | $O{-}\text{Ph}$ | 145–7 |

TABLE 1-continued

Structure: tetrahydrophthalimide with N-phenyl bearing $R_1$ (6), $R_2$ (4), CO-Z (3); $R_3$ on cyclohexene ring.

| No. | $R_1$ | $R_2$ | $R_3$ | Z | m.p. (°C.) or refractive index |
|---|---|---|---|---|---|
| 23 | " | " | " | $SC_2H_5$ | 74–8 |
| 24 | " | " | " | $SC_3H_7(i)$ | 103–5 |
| 25 | 4-Br | H | " | OH | 239–240 |
| 26 | " | " | " | $OCH_3$ | 99–101 |
| 27 | " | " | " | $OC_2H_5$ | $n_D^{25}$ 1.5662 |
| 28 | " | " | " | $OC_3H_7(n)$ | $n_D^{25}$ 1.5625 |
| 29 | " | " | " | $OC_3H_7(i)$ | 80–3 |
| 30 | " | " | " | $OC_4H_9(sec)$ | $n_D^{25}$ 1.5521 |
| 31 | " | " | " | $OC_5H_{11}(sec)$ | $n_D^{25}$ 1.5464 |
| 32 | " | " | " | $OCH(CH(CH_3)_2)CH_3$ (OCH CH CH$_3$ / CH$_3$CH$_3$) | $n_D^{25}$ 1.5498 |
| 33 | " | " | " | $OCH(C_2H_5)CH_2CH_3$ | $n_D^{25}$ 1.5504 |
| 34 | " | " | " | $OCH(C_2H_5)(CH_2)_3CH_3$ | $n_D^{25}$ 1.5542 |
| 35 | " | " | " | $OCHCH_2CHCH_3$ / $CH_3$ $CH_3$ | $n_D^{25}$ 1.5402 |
| 36 | " | " | " | $OCH(C_2H_5)(CH_2)_2CH_3$ | $n_D^{25}$ 1.5478 |
| 37 | " | " | " | $OCH(C_2H_5)(CH_2)_3CH_3$ | $n_D^{25}$ 1.5380 |
| 38 | 4-$CH_3$ | " | " | OH | 237–8 |
| 39 | " | " | " | $OCH_3$ | 104–5 |
| 40 | " | " | " | $OC_2H_5$ | 143–5 |
| 41 | " | " | " | $OC_3H_7(n)$ | 106–7 |
| 42 | " | " | " | $OC_3H_7(i)$ | 95–6 |
| 43 | " | " | " | $OC_4H_9(sec)$ | 88–90 |
| 44 | " | " | " | $OC_5H_{11}(sec)$ | 80–2 |
| 45 | " | " | " | OCH CH $CH_3$ / $CH_3$CH$_3$ | $n_D^{25}$ 1.5383 |
| 46 | " | 6-$CH_3$ | " | OH | 248–252 |
| 47 | " | " | " | $OC_2H_5$ | 74–6 |
| 48 | " | " | " | $OC_3H_7(i)$ | 84–7 |
| 49 | " | " | " | $OC_4H_9(sec)$ | $n_D^{25}$ 1.5465 |
| 50 | 4-$OCH_3$ | H | " | $OCH_3$ | 124.5–5.5 |
| 51 | 4-$OCH_2CH_3$ | " | " | $OCH_3$ | 129–9.5 |
| 52 | 4-$OCH_2$—$CH_2CH_3$ | " | " | OH | 189–190 |
| 53 | " | " | " | $OCH_3$ | 85–6 |
| 54 | " | " | " | $OC_6H_7(i)$ | 94–5 |
| 55 | 6-F | " | " | OH | 243–5 |
| 56 | 6-F | " | " | $OC_3H_7(i)$ | $n_D^{25}$ 1.5346 |
| 57 | 4-F | " | " | $OCH_3$ | 92–3.5 |
| 58 | " | " | " | $OC_2H_5$ | 83.5–4.5 |
| 59 | " | " | " | $OC_3H_7(i)$ | 69–71.5 |
| 60 | " | " | " | $OC_4H_9(n)$ | $n_D^{25}$ 1.5445 |
| 61 | 2-Cl | 5-Cl | " | $OC_2H_5$ | 133–6 |
| 62 | 2-$NO_2$ | H | " | $OC_2H_5$ | 117.5–9.5 |
| 63 | 4-Cl | 6-F | " | $OC_2H_5$ | 92–5 |
| 64 | " | " | " | $OC_3H_7(i)$ | $n_D^{25}$ 1.5482 |
| 65 | " | " | " | $OC_4H_9(sec)$ | $n_D^{25}$ 1.5460 |
| 66 | " | 6-Cl | " | $O(CH_2)_2OCH_3$ | $n_D^{25}$ 1.5736 |
| 67 | " | " | " | $O(CH_2)_2OC_2H_5$ | $n_D^{25}$ 1.5530 |
| 68 | 4-F | H | " | $O^-Na^+$ | >280 |
| 69 | 4-Cl | 6-Cl | " | $O^-Na^+$ | >270 |
| 70 | " | " | " | $O^-K^+$ | dec 235–50 |

TABLE 1-continued

| No. | $R_1$ | $R_2$ | $R_3$ | Z | m.p. (°C.) or refractive index |
|---|---|---|---|---|---|
| 71 | " | " | " | O−½ Ca++ | >270 |
| 72 | " | " | " | O−½ Mn++ | >270 |
| 73 | 4-Br | H | " | $NH_2$ | 221–4 |
| 74 | " | " | " | NHCH(OH)CCl$_3$ | 138–40 |
| 75 | " | " | " | NHCH=C(Cl)(Cl) | 160–3 |
| 76 | 4-Cl | 6-Cl | " | $NHCH_3$ | 88–91 |
| 77 | " | " | " | $NHC_2H_5$ | 89–94 |
| 78 | " | " | " | $NHC_3H_7(i)$ | 202–4 |
| 79 | " | " | " | $N(CH_3)_2$ | 154–7 |
| 80 | " | " | " | morpholino (N−O ring) | 168–171.5 |
| 81 | " | " | " | $NHC_4H_9(sec)$ | $n_D^{25}$ 1.5484 |
| 82 | " | " | " | $NHCH_2CH(C_2H_5)(CH_2)_3CH_3$ | 85–87 |
| 83 | " | " | " | $NHCH_2CH=CH_2$ | 69–71 |
| 84 | 4-Cl | " | $CH_3$* | $OC_2H_5$ | $n_D^{25}$ 1.5484 |
| 85 | " | " | " | $OC_3H_7(i)$ | $n_D^{25}$ 1.5530 |
| 86 | " | " | " | $OC_4H_9(sec)$ | $n_D^{25}$ 1.5521 |
| 87 | " | " | " | $OC_5H_{11}(sec)$ | $n_D^{25}$ 1.5456 |
| 88 | 4-Br | 6-F | " | $OC_3H_7(i)$ | $n_D^{25}$ 1.5531 |
| 89 | " | " | H | $OC_2H_5$ | 107–109.5 |
| 90 | " | " | " | $OC_3H_7(n)$ | $n_D^{25}$ 1.5670 |
| 91 | " | " | " | $OC_4H_9(n)$ | $n_D^{25}$ 1.5618 |
| 92 | " | " | " | $OC_4H_9(sec)$ | $n_D^{25}$ 1.5605 |
| 93 | " | " | " | $OC_5H_{11}(n)$ | $n_D^{25}$ 1.5545 |
| 94 | " | " | " | $OC_5H_{11}(sec)$ | $n_D^{25}$ 1.5550 |
| 95 | " | " | " | $OCH(CH_2CH_3)(CH_3)$ | $n_D^{25}$ 1.5565 |
| 96 | " | " | " | $OCHCH_2CH(CH_3)_2 \cdot CH_3$ | $n_D^{25}$ 1.5472 |
| 97 | 4-Cl | " | " | $OC_3H_7(n)$ | $n_D^{25}$ 1.5431 |
| 98 | " | " | " | $OC_4H_9(n)$ | $n_D^{25}$ 1.5464 |
| 99 | " | " | " | $OC_5H_{11}(n)$ | $n_D^{25}$ 1.5413 |
| 100 | " | " | " | $OC_5H_{11}(sec)$ | $n_D^{25}$ 1.5365 |
| 101 | " | " | " | $OCH(CH_2CH_3)CH_3$ | $n_D^{25}$ 1.5320 |
| 102 | " | " | " | $O-CH(CH_3)-CH_2CH(CH_3)-CH_3$ | $n_D^{25}$ 1.5330 |
| 103 | " | " | 4-$CH_3$ | $O-C_3H_7(i)$ | $n_D^{25}$ 1.5338 |
| 104 | " | " | " | $O-C_4H_9(sec)$ | $n_D^{25}$ 1.5315 |
| 105 | 4-Br | " | H | OH | 215–6 |
| 106 | " | H | 3-$CH_3$ | $O-C_3H_7(i)$ | 97–8 |
| 107 | 4-Cl | " | 4-$CH_3$ | $OCH_3$ | 106–110 |
| 108 | " | " | " | $OC_2H_5$ | 73–5 |
| 109 | " | " | " | $OC_3H_7(i)$ | 87–90 |

TABLE 1-continued

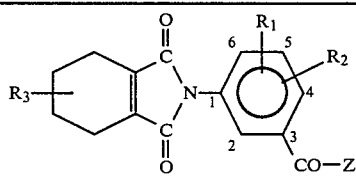

| No. | $R_1$ | $R_2$ | $R_3$ | Z | m.p. (°C.) or refractive index |
|---|---|---|---|---|---|
| 110 | " | " | " | $OC_3H_7(n)$ | 51-4 |
| 111 | " | " | " | $OC_4H_9(sec)$ | 53-5 |
| 112 | " | " | " | $OCHCH_2CH\!-\!CH_3$<br>$\quad\|\qquad\quad\|$<br>$\;CH_3\quad\;\;CH_3$ | 59-62 |
| 113 | " | 6-Cl | " | $OC_4H_9(sec)$ | $n_D^{25}1.5570$ |
| 114 | 4-Br | 6-F | " | $OC_3H_7(i)$ | $n_D^{25}1.5520$ |
| 115 | 4-Cl | H | 3-$CH_3$ | $OC_3H_7(i)$ | 96-9 |
| 116 | " | 6-Cl | " | $OC_3H_7(i)$ | $n_D^{25}1.5521$ |
| 117 | " | 6-F | H | OH | 194-7 |
| 118 | " | H | " | $O\!-\!CH\!-\!CH_3$<br>$\qquad\;\|$<br>$\qquad CN$ | 110-111.5 |
| 119 | " | " | " | $OCH_2CH_2CN$ | 99-101 |
| 120 | " | " | " | $O\!-\!CH(CH_2)_2CH_3$<br>$\qquad\;\|$<br>$\qquad CN$ | 75-79 |
| 121 | " | " | " | $O\!-\!CH\!-\!(CH_2)_5CH_3$<br>$\qquad\;\|$<br>$\qquad CN$ | $n_D^{25}1.5120$ |
| 122 | " | 6-F | " | $O\!-\!CH\!-\!CH_3$<br>$\qquad\;\|$<br>$\qquad CN$ | 111-112.5 |
| 123 | " | " | " | $O\!-\!CH_2CH_2CN$ | 45-47 |
| 124 | 4-Br | H | " | $O\!-\!CHC_2H_5$<br>$\qquad\;\|$<br>$\qquad CN$ | 55-59 |
| 125 | " | " | " | $O\!-\!CH\!-\!CH_2CH\!-\!CH_3$<br>$\qquad\;\|\qquad\qquad\;\;\|$<br>$\qquad CN\qquad\quad CH_3$ | $n_D^{25}1.5521$ |

*$CH_3$ means mixture (3-$CH_3$:4-$CH_3$ = 25:75)

Furthermore the compounds of the following formula obtained by the methods of synthesis examples 1–9 are shown in Table 2.

TABLE 2

| No. | R | Z | m.p. (°C.) or refractive index |
|---|---|---|---|
| 126 | H | $OCH_3$ | 123-5 |
| 127 | " | $OCH_2CH_3$ | 72-5 |
| 128 | " | $CH_3$<br>$\;\|$<br>$OCHCH_3$ | 84-5 |
| 129 | " | $OCH_2CH_2Cl$ | 64-6 |

TABLE 2-continued

| No. | R | Z | m.p. (°C.) or refractive index |
|---|---|---|---|
| 130 | " | $CH_2Cl$<br>$\;\|$<br>$OCHCH_2Cl$ | 100-2 |
| 131 | " | $CH_3$<br>$\;\|$<br>$OCHCH_2CH_3$ | $n_D^{25}$ 1.5470 |
| 132 | " | $CH_3$<br>$\;\|$<br>$OCCH_3$<br>$\;\|$<br>$CH_3$ | 124-6 |

TABLE 2-continued

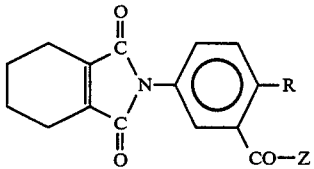

| No. | R | Z | m.p. (°C.) or refractive index |
|---|---|---|---|
| 133 | " | CH₃–OCH–CH₂CH₂CH₃ | $n_D^{25}$ 1.5372 |
| 134 | " | (CH₃)(CH₃)OCH–CHCH₃ | $n_D^{25}$ 1.5441 |
| 135 | " | CH₃–OCC(CH₃)CH₂CH₃ (OCC(CH₃)₂CH₂CH₃) | 120–4 |
| 136 | " | CH₂CH₃–OCHCH₂CH₃ | $n_D^{25}$ 1.5361 |
| 137 | " | OCH₂CH₂CH₂CH₂CH₃ | $n_D^{25}$ 1.5443 |
| 138 | " | (CH₃)(CH₃)OCHCH₂CH–CH₃ | 66–8 |
| 139 | " | CH₂CH₃–OCHCH₂CH₂CH₃ | $n_D^{25}$ 1.5365 |
| 140 | " | CH₃–OCHCH₂CH₂CH₂CH₃ | $n_D^{25}$ 1.5300 |
| 141 | " | CH₂CH₃–OCHCH₂CH₂CH₃ | $n_D^{25}$ 1.5250 |
| 142 | " | CH₂CH₃–OCHCH₂CH₂CH₂CH₃ | $n_D^{25}$ 1.5309 |
| 143 | " | CH₃–OCHCH₂CH₂CH₂CH₂CH₃ | $n_D^{25}$ 1.4800 |
| 144 | " | (CH₃)(CH₃)OCH₂CCH₂CHCH₃ (with CH₃) | 68–9 |
| 145 | Cl | OH | 245.5–6.5 |
| 146 | " | OCH₃ | 123–3.5 |
| 147 | " | OCH₂CH₃ | 95 |
| 148 | " | OCH₂CH₂CH₃ | 58–9 |
| 149 | " | CH₃–OCHCH₃ | 85–85.5 |
| 150 | " | O–CH₂CH₂CH₂CH₃ | $n_D^{25}$ 1.5640 |
| 151 | " | CH₃–OCH₂CHCH₃ | $n_D^{25}$ 1.5615 |
| 152 | " | CH₃–OCHCH₂CH₃ | $n_D^{25}$ 1.5515 |
| 153 | " | CH₃–OCCH₃–CH₃ | 122.5–4 |
| 154 | " | OCH₂CH₂CH₂CH₂CH₃ | $n_D^{25}$ 1.5528 |
| 155 | " | CH₃–OCHCH₂CH₂CH₃ | $n_D^{25}$ 1.5540 |
| 156 | " | (CH₃)(CH₃)OCH–CHCH₃ | $n_D^{25}$ 1.5509 |
| 157 | " | OCH₂CH₂Cl | 96–8° C. |
| 158 | " | CH₃–OCCH₂CH₃–CH₃ | 123–4° C. |
| 159 | " | (CH₃)(CH₃)OCHCH₂CH₃ | $n_D^{25}$ 1.5553 |
| 160 | " | OCH₂CH₂CH₂CH₂CH₂CH₃ | $n_D^{25}$ 1.5509 |
| 161 | " | CH₃–OCHCH₂CH₂CH₃ | $n_D^{25}$ 1.5492 |
| 162 | " | (CH₃)(CH₃)OCHCH₂CHCH₃ | $n_D^{25}$ 1.5429 |
| 163 | " | CH₂CH₃–OCHCH₂CH₃ | 58–60 |
| 164 | " | CH₂CH₃–OCHCH₂CH₂CH₃ | $n_D^{25}$ 1.5459 |
| 165 | " | CH₂CH₃–OCHCH₂CH₂CH₂CH₃ | $n_D^{25}$ 1.5380 |
| 166 | " | CH₃–OCHCH₂CH₂CH₂CH₂CH₃ | $n_D^{25}$ 1.5408 |
| 167 | " | (CH₃)(CH₃)OCH₂CCH₂CHCH₃ (with CH₃) | $n_D^{25}$ 1.5452 |
| 168 | " | OCH₂CH=CH₂ | 60–1.5 |
| 169 | " | OCH₂C≡CH | 124.5–5 |
| 170 | " | CH₃–OCH₂CH₂CH–CH₃ | 36–8 |
| 171 | " | S C₂H₅ | 117–7.5 |
| 172 | " | NH₂ | 237–40 |
| 173 | " | NHCH₂CH₃ | 124.5–6 |
| 174 | " | NHCH₂CH₂CH₃ | 139–40 |
| 175 | " | N(CH₃)₂ | 173–4 |

TABLE 2-continued

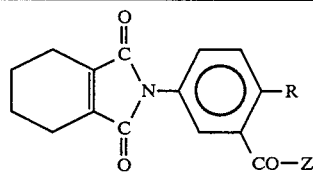

| No. | R | Z | m.p. (°C.) or refractive index |
|---|---|---|---|
| 176 | " | N(C$_2$H$_5$)$_2$ | 103.5–4.5 |
| 177 | " | NHCH$_2$CH=CH$_2$ | 131–2 |
| 178 | " | O$^-$Na$^+$ | >280 |
| 179 | " | O$^-$K$^+$ | 245 |
| 180 | " | O$^-\frac{1}{2}$Ca$^{++}$ | >280 |
| 181 | " | O$^-\frac{1}{2}$Mn$^{++}$ | dec. 225– |

The herbicidal composition of the present invention can be used either alone or in the form of a formulation according to the purpose of its use. To promote or secure the effect, it is mixed with adjuvants to make formulations such as dust, micro granule, granule, wettable powder, flowable suspension concentrates and emulsion by means of usual procedures. These formulations are used, at the time of practical application, in the form as they are or diluted with water to desired concentration.

Those adjuvants mentioned above include carriers (diluents), extending agents, emusfiers, wetting agents, dispersing agents, fixing agents and disintegrators.

As liquid carriers there can be used water, aromatic hydrocarbons such as toluene and xylene, alcohols such as methanol, butanol and glycol, ketones such as acetone, amides such as dimethylformamide, sulfoxides such as dimethylsulfoxide, methylnaphthalene, cyclohexane, animal and vegetable oils, fatty acids and their esters, etc. As solid carriers are used clay, kaolin, talc, diatomaceous earth, silica, calcium carbonate, montmorillonite, bentonite, feldspar, quartz, alumina, sawdust, etc.

As emulsifiers or dispersing agents surfactants are generally used. They include anionic, cationic, nonionic and amphoteric surfactants such as sodium salts of sulfated higher alcohol, steariltrimethylammonium chloride, polyoxyethylenealkylphenylether and lauryl betaine. Wetting agents include sodium alkylnaphthalene sulfonate and ammonium polyoxyethylenealkylphenylether sulfate, fixing agents include polyvinyl alcohol, polyvinyl acetate and CMC, and disintegrators include sodium lignin sulfonate.

Any type of said formulations can not only used alone, but also may be mixed with fungicides, insecticides, plant growth regulators, acaricides, soil modifying agents or nematocides and further can be used in combination with fertilizers or other herbicides.

The content of a compound (active ingredient) of the present invention in the formulations varies with types of formulation, methods of application and other conditions, but generally it is 0.1 to 95 weight %, preferably 0.2 to 50 weight %, while the content of adjuvants is 5 to 99.9 weight %, preferably 50 to 99.8 weight %, though sometimes the compound can be used alone. To be more precise, a preferable range of the content is shown as under.

| | Compound (weight %) | Adjuvant (weight %) |
|---|---|---|
| Dust | 0.2–10 | 90–99.8 |
| Emulsion | 20–80 | 20–80 |
| Wettable powder | 20–80 | 20–80 |
| Granule and micro granule | 0.2–20 | 80–99.8 |
| Flowable suspension concentrate | 20–80 | 20–80 |

A quantity to use of the formulations is different with kinds of the active ingredient and places of application, but generally it is within the range of 1 to 100 g, preferably 3 to 75 g, of the compound per are.

Detailed explanation will be made below on examples of formulations of the present invention and there the word "part" means part by weight.

Formulation Example 1: Emulsion 35 parts of a mixture (1:1) of xylene and methylnaphthalene are added to 50 parts of Compound No. 7 to dissolve and the solution is further mixed with 15 parts of a mixture (8:2) of polyoxyethylenealkylphenylether and calcium alkylbenzenesulfonate to obtain an emulsion. It is diluted with water to use in a concentration of 0.01 to 1%.

Formulation Example 2: Dust 5 parts of Compound No. 23 are mixed with 95 parts of clay and pulverized to obtain a dust. It is directly used for dusting.

Formulation Example 3: Wettable powder 50 parts of Compound No. 25 are mixed with 10 parts of diatomaceous earth and 32 parts of kaolin and further uniformly blended with 8 parts of a mixture of sodium laurylsulfate and sodium 2,2'-dinaphthylmethanesulfonate, and finely pulverized to obtain a wettable powder. It is used in the form of a suspension by diluting to a concentration of 0.06 to 1%.

Formulation Example 4: Granule 5 parts of a fine dust of Compound No. 24 are extended for coating on 94.5 parts of grains (16 to 32 mesh) of silica to obtain a granule, by using a methanol solution of 0.5 parts of polyvinyl polyacetate as the binding agent in a proper mixer. The granule is scattered directly in up-land field and a paddy field.

Formulation Example 5: Flowable suspension concentrates 40 parts of a fine powder of Compound 24, 10 parts of ethyleneglycolmonobutylether, 10 parts of a surfactant (mixture of trioxyalkylether, polyoxyethylenenonylphenylether and sodium alkylarylsulfonate), 3 parts of colloidal aluminium silicate hydrate and 22 parts of water are uniformly mixed and further blended under stirring in a homomixer for 20 minutes to obtain a flowable. It is diluted with water for use in a concentration of 0.02 to 1%.

The excellent herbicidal activity of a compound of the present invention will be illustrated in the following test examples.

Each test was carried out on 2-replication system and the test results are given in the average value.

Test Example 1: Pre-emergence treatment in flooded condition

A fixed amount of paddy field soil was filled in each Wagner pot sized 1/5,000 are to provide a condition similar to a paddy field and there was sown a fixed amount of seeds of barnyard grass, monochoria, toothcup, false pimpernal, water wort and umbrella plant.

In addition tubers of arrowhead were buried 1 cm under the surface of soil at the rate of 3 pieces per pot and the pot was flooded with water 3 cm deep. Then the pot was applied with a diluted solution of the compound of the present invention at a rate of 6.25 to 50 g of the compound of the present invention per are.

After three days 3 pieces of rice seedlings (variety: Nihonbare) in 2.5-leaf stage were transplanted from a nursery to each pot. Thirty days after the treatment the herbicidal activity and the phytotoxicity against paddy rice were observed. The test results were classified on the following basis as shown in Table 3.

| Herbicidal activity index: | |
|---|---|
| 5 | Complete weeding |
| 4 | up to 80% weeding |
| 3 | up to 60% weeding |
| 2 | up to 40% weeding |
| 1 | up to 20% weeding |
| 0 | no effect |

| Phytotoxicity index: | |
|---|---|
| − | no damage |
| + | slight damage |
| ++ | some damage |
| +++ | moderate damage |
| ++++ | heavy damage |
| × | complete death |

TABLE 3

Test Example 1: Pre-emergence treatment under flooded condition

| Compound No. | Dosage g/a | Barnyard grass | Broad leaf (1) | Umbrella plant | Arrowheed | Phytotoxicity against paddy rice |
|---|---|---|---|---|---|---|
| 1 | 50 | 4 | 5 | 5 | 5 | + |
|  | 25 | 2 | 5 | 5 | 5 | ± |
|  | 12.5 | 2 | 4.5 | 5 | 3 | − |
| 2 | 25 | 5 | 5 | 5 | 3 | ± |
|  | 12.5 | 4.5 | 5 | 5 | 2 | − |
|  | 6.25 | 4 | 5 | 5 | 2 | − |
| 3 | 25 | 5 | 5 | 5 | 5 | + |
|  | 12.5 | 5 | 5 | 5 | 5 | + |
|  | 6.25 | 5 | 5 | 5 | 5 | ± |
| 4 | 25 | 5 | 5 | 5 | 4.5 | ± |
|  | 12.5 | 5 | 5 | 5 | 3.5 | − |
|  | 6.25 | 3.5 | 5 | 5 | 2 | − |
| 5 | 25 | 5 | 5 | 5 | 5 | + |
|  | 12.5 | 5 | 5 | 5 | 5 | ± |
|  | 6.25 | 5 | 5 | 5 | 4 | − |
| 6 | 25 | 5 | 5 | 5 | 4 | − |
|  | 12.5 | 3 | 4 | 5 | 2.5 | − |
|  | 6.25 | 2 | 3.5 | 4 | 2 | − |
| 7 | 25 | 5 | 5 | 5 | 5 | ± |
|  | 12.5 | 5 | 5 | 5 | 5 | − |
|  | 6.25 | 5 | 5 | 5 | 4 | − |
| 8 | 25 | 5 | 5 | 5 | 5 | + |
|  | 12.5 | 5 | 5 | 5 | 5 | ± |
|  | 6.25 | 5 | 5 | 5 | 5 | ± |
| 9 | 25 | 5 | 5 | 5 | 3.5 | ± |
|  | 12.5 | 5 | 5 | 5 | 2 | − |
|  | 6.25 | 5 | 5 | 5 | 2 | − |
| 10 | 25 | 5 | 5 | 5 | 5 | + |
|  | 12.5 | 5 | 5 | 5 | 5 | ± |
|  | 6.25 | 5 | 5 | 5 | 5 | − |
| 11 | 25 | 5 | 5 | 5 | 5 | + |
|  | 12.5 | 5 | 5 | 5 | 5 | ± |
|  | 6.25 | 5 | 5 | 5 | 3 | − |
| 12 | 25 | 5 | 5 | 5 | 5 | − |
|  | 12.5 | 5 | 5 | 5 | 4.5 | − |
|  | 6.25 | 3.5 | 5 | 5 | 3 | − |
| 13 | 25 | 5 | 5 | 5 | 5 | ± |
|  | 12.5 | 5 | 5 | 5 | 4.5 | − |
|  | 6.25 | 5 | 5 | 5 | 3 | − |
| 14 | 25 | 5 | 5 | 5 | 4 | ± |
|  | 12.5 | 5 | 5 | 5 | 3.5 | ± |
|  | 6.25 | 5 | 5 | 5 | 3 | − |
| 15 | 25 | 5 | 5 | 5 | 3.5 | − |
|  | 12.5 | 5 | 5 | 5 | 3 | − |
|  | 6.25 | 5 | 5 | 5 | 2 | − |
| 16 | 25 | 4.5 | 5 | 5 | 3 | − |
|  | 12.5 | 3 | 5 | 5 | 2 | − |
|  | 6.25 | 2 | 5 | 5 | 2 | − |
| 17 | 25 | 5 | 5 | 5 | 3 | − |
|  | 12.5 | 4.5 | 5 | 5 | 2.5 | − |
|  | 6.25 | 4 | 5 | 5 | 2 | − |
| 18 | 50 | 5 | 5 | 5 | 3.5 | − |
|  | 25 | 3.5 | 5 | 5 | 2.5 | − |
|  | 12.5 | 2 | 5 | 5 | 2 | − |
| 19 | 50 | 3 | 5 | 4.5 | 3.5 | − |
|  | 25 | 2 | 3.5 | 3.5 | 2 | − |
|  | 12.5 | 2 | 2 | 2 | 2 | − |
| 20 | 25 | 5 | 5 | 5 | 5 | − |
|  | 12.5 | 4.5 | 5 | 5 | 4 | − |
|  | 6.25 | 3 | 4.5 | 4.5 | 2 | − |
| 21 | 50 | 3.5 | 5 | 5 | 3 | − |
|  | 25 | 2.5 | 5 | 5 | 2 | − |
|  | 12.5 | 2 | 5 | 5 | 2 | − |
| 22 | 25 | 4 | 5 | 5 | 3 | − |
|  | 12.5 | 3 | 5 | 5 | 2.5 | − |
|  | 6.25 | 2 | 5 | 5 | 2 | − |
| 23 | 25 | 5 | 5 | 5 | 5 | ± |
|  | 12.5 | 5 | 5 | 5 | 3.5 | − |
|  | 6.25 | 5 | 5 | 5 | 3 | − |
| 24 | 25 | 5 | 5 | 5 | 3.5 | − |
|  | 12.5 | 5 | 5 | 5 | 2.5 | − |
|  | 6.25 | 5 | 5 | 5 | 2 | − |
| 25 | 50 | 3.5 | 5 | 5 | 5 | ± |
|  | 25 | 2.5 | 5 | 5 | 5 | − |
|  | 12.5 | 2 | 5 | 5 | 5 | − |
| 26 | 25 | 5 | 5 | 5 | 5 | + |
|  | 12.5 | 5 | 5 | 5 | 5 | ± |
|  | 6.25 | 5 | 5 | 5 | 4.5 | − |
| 27 | 25 | 5 | 5 | 5 | 5 | ± |
|  | 12.5 | 5 | 5 | 5 | 5 | − |
|  | 6.25 | 5 | 5 | 5 | 4 | − |
| 28 | 25 | 5 | 5 | 5 | 5 | ± |
|  | 12.5 | 5 | 5 | 5 | 5 | − |
|  | 6.25 | 5 | 5 | 5 | 3.5 | − |
| 29 | 25 | 5 | 5 | 5 | 5 | ± |
|  | 12.5 | 5 | 5 | 5 | 5 | − |
|  | 6.25 | 5 | 5 | 5 | 5 | − |
| 30 | 25 | 5 | 5 | 5 | 5 | + |
|  | 12.5 | 5 | 5 | 5 | 4 | ± |
|  | 6.25 | 5 | 5 | 5 | 3 | − |
| 31 | 25 | 5 | 5 | 5 | 5 | + |
|  | 12.5 | 5 | 5 | 5 | 3.5 | − |
|  | 6.25 | 5 | 5 | 5 | 2.5 | − |
| 32 | 25 | 5 | 5 | 5 | 4 | ± |
|  | 12.5 | 5 | 5 | 5 | 3 | ± |
|  | 6.25 | 5 | 5 | 5 | 2 | − |
| 33 | 25 | 5 | 5 | 5 | 5 | + |
|  | 12.5 | 5 | 5 | 5 | 3 | − |
|  | 6.25 | 5 | 5 | 5 | 2 | − |
| 34 | 25 | 5 | 5 | 5 | 5 | ± |
|  | 12.5 | 5 | 5 | 5 | 5 | ± |
|  | 6.25 | 5 | 5 | 5 | 4 | − |
| 35 | 25 | 5 | 5 | 5 | 5 | ± |
|  | 12.5 | 5 | 5 | 5 | 4.5 | − |
|  | 6.25 | 5 | 5 | 5 | 2 | − |
| 36 | 25 | 5 | 5 | 5 | 3.5 | − |

TABLE 3-continued

Test Example 1: Pre-emergence treatment under flooded condition

| Compound No. | Dosage g/a | Barn-yard grass | Broad leaf (1) | Um-brella plant | Arrow-head | Phyto-toxicity against paddy rice |
|---|---|---|---|---|---|---|
| | 12.5 | 5 | 5 | 5 | 3 | — |
| | 6.25 | 5 | 5 | 5 | 2 | — |
| 37 | 25 | 5 | 5 | 5 | 3.5 | ± |
| | 12.5 | 5 | 5 | 5 | 2.5 | — |
| | 6.25 | 5 | 5 | 5 | 2 | — |
| 38 | 50 | 3 | 5 | 5 | 5 | ± |
| | 25 | 2.5 | 5 | 5 | 4.5 | — |
| | 12.5 | 2 | 5 | 5 | 4 | — |
| 39 | 25 | 5 | 5 | 5 | 5 | + |
| | 12.5 | 5 | 5 | 5 | 5 | + |
| | 6.25 | 5 | 5 | 5 | 5 | — |
| 40 | 25 | 5 | 5 | 5 | 5 | + |
| | 12.5 | 5 | 5 | 5 | 5 | + |
| | 6.25 | 5 | 5 | 5 | 4 | ± |
| 41 | 25 | 5 | 5 | 5 | 5 | + |
| | 12.5 | 5 | 5 | 5 | 4 | ± |
| | 6.25 | 5 | 5 | 5 | 3 | — |
| 42 | 25 | 5 | 5 | 5 | 5 | + |
| | 12.5 | 5 | 5 | 5 | 5 | ± |
| | 6.25 | 5 | 5 | 5 | 4.5 | — |
| 43 | 25 | 5 | 5 | 5 | 5 | + |
| | 12.5 | 5 | 5 | 5 | 5 | + |
| | 6.25 | 5 | 5 | 5 | 4.5 | — |
| 44 | 25 | 5 | 5 | 5 | 5 | ± |
| | 12.5 | 5 | 5 | 5 | 5 | — |
| | 6.25 | 5 | 5 | 5 | 4.5 | — |
| 45 | 25 | 5 | 5 | 5 | 5 | + |
| | 12.5 | 5 | 5 | 5 | 5 | ± |
| | 6.25 | 5 | 5 | 5 | 4.5 | — |
| 46 | 50 | 3 | 5 | 5 | 2 | — |
| | 25 | 2.5 | 5 | 5 | 2 | — |
| | 12.5 | 2 | 5 | 5 | 2 | — |
| 47 | 25 | 5 | 5 | 5 | 5 | ± |
| | 12.5 | 5 | 5 | 5 | 5 | — |
| | 6.25 | 5 | 5 | 5 | 3.5 | — |
| 48 | 25 | 5 | 5 | 5 | 4 | ± |
| | 12.5 | 5 | 5 | 5 | 3 | — |
| | 6.25 | 5 | 5 | 5 | 2 | — |
| 49 | 25 | 5 | 5 | 5 | 4 | — |
| | 12.5 | 5 | 5 | 5 | 3 | — |
| | 6.25 | 5 | 5 | 5 | 2 | — |
| 50 | 25 | 4 | 5 | 5 | 3 | — |
| | 12.5 | 3 | 5 | 5 | 2 | — |
| | 6.25 | 2 | 4 | 4 | 2 | — |
| 51 | 50 | 3 | 5 | 5 | 3 | — |
| | 25 | 2.5 | 4 | 3 | 2 | — |
| | 12.5 | 2 | 3 | 3 | 2 | — |
| 53 | 50 | 4.5 | 5 | 5 | 2 | — |
| | 25 | 2 | 3 | 3 | 1 | — |
| 54 | 50 | 4.5 | 5 | 5 | 3.5 | — |
| | 25 | 3 | 5 | 5 | 2 | — |
| | 12.5 | 2.5 | 5 | 5 | 1 | — |
| 55 | 25 | 3 | 5 | 5 | 5 | — |
| | 12.5 | 2.5 | 5 | 5 | 4 | — |
| | 6.25 | 2 | 5 | 5 | 3 | — |
| 56 | 25 | 5 | 5 | 5 | 5 | + |
| | 12.5 | 5 | 5 | 5 | 5 | ± |
| | 6.25 | 5 | 5 | 5 | 5 | — |
| 57 | 50 | 3 | 5 | 5 | 3 | — |
| | 25 | 2 | 5 | 4 | 2 | — |
| | 12.5 | 1 | 2 | 3 | 1 | — |
| 58 | 50 | 5 | 5 | 5 | 3 | — |
| | 25 | 4 | 5 | 5 | 2 | — |
| | 12.5 | 2 | 3 | 3 | 2 | — |
| 59 | 25 | 5 | 5 | 5 | 3 | ± |
| | 12.5 | 4.5 | 5 | 5 | 2.5 | — |
| | 6.25 | 3 | 4 | 5 | 2 | — |
| 60 | 50 | 4 | 5 | 5 | 3 | — |
| | 25 | 3 | 5 | 5 | 2 | — |
| 61 | 25 | 5 | 5 | 5 | 3 | — |
| | 12.5 | 4 | 5 | 4 | 2 | — |
| | 6.25 | 3 | 4 | 3 | 2 | — |
| 63 | 25 | 5 | 5 | 5 | 5 | + |
| | 12.5 | 5 | 5 | 5 | 5 | ± |
| | 6.25 | 5 | 5 | 5 | 5 | — |
| 64 | 25 | 5 | 5 | 5 | 5 | + |
| | 12.5 | 5 | 5 | 5 | 5 | ± |
| | 6.25 | 5 | 5 | 5 | 5 | — |
| 65 | 25 | 5 | 5 | 5 | 5 | + |
| | 12.5 | 5 | 5 | 5 | 5 | ± |
| | 6.25 | 5 | 5 | 5 | 5 | — |
| 66 | 25 | 5 | 5 | 5 | 5 | + |
| | 12.5 | 4.5 | 5 | 5 | 5 | ± |
| | 6.25 | 3 | 5 | 5 | 4 | — |
| 67 | 25 | 5 | 5 | 5 | 5 | + |
| | 12.5 | 4.5 | 5 | 5 | 5 | ± |
| | 6.25 | 2.5 | 5 | 5 | 4 | — |
| 68 | 50 | 3 | 5 | 4 | 3 | — |
| | 25 | 2 | 5 | 3.5 | 2 | — |
| 69 | 50 | 3 | 5 | 5 | 5 | ± |
| | 25 | 2 | 5 | 5 | 5 | — |
| | 12.5 | 2 | 3 | 5 | 2 | — |
| 71 | 50 | 3 | 5 | 5 | 5 | ± |
| | 25 | 2 | 5 | 5 | 4 | — |
| | 12.5 | 2 | 5 | 5 | 2.5 | — |
| 72 | 50 | 3 | 5 | 5 | 5 | ± |
| | 25 | 2 | 5 | 5 | 3 | — |
| 73 | 50 | 5 | 5 | 5 | 5 | + |
| | 25 | 3.5 | 5 | 5 | 5 | ± |
| | 12.5 | 2 | 5 | 5 | 3 | — |
| 74 | 50 | 4 | 5 | 5 | 4 | ± |
| | 25 | 3.5 | 5 | 5 | 3 | — |
| | 12.5 | 2 | 5 | 5 | 2 | — |
| 75 | 50 | 3 | 5 | 5 | 2 | — |
| | 25 | 2 | 3 | 3 | 1.5 | — |
| 76 | 50 | 5 | 5 | 5 | 5 | + |
| | 25 | 4.5 | 5 | 5 | 3 | — |
| | 12.5 | 3 | 5 | 5 | 2 | — |
| 77 | 50 | 5 | 5 | 5 | 4.5 | ++ |
| | 25 | 4.5 | 5 | 5 | 3 | + |
| | 12.5 | 3 | 5 | 5 | 2 | — |
| 78 | 25 | 4.5 | 5 | 5 | 3.5 | ± |
| | 12.5 | 4 | 5 | 5 | 2 | — |
| 79 | 50 | 5 | 5 | 5 | 3 | — |
| | 25 | 4 | 5 | 5 | 2 | — |
| | 12.5 | 3 | 5 | 5 | 2 | — |
| 80 | 50 | 3 | 5 | 5 | 3 | — |
| | 25 | 2 | 5 | 5 | 2 | — |
| 81 | 50 | 5 | 5 | 5 | 4 | ± |
| | 25 | 4 | 5 | 5 | 2 | — |
| | 12.5 | 2 | 5 | 5 | 2 | — |
| 82 | 25 | 4.5 | 5 | 5 | 3 | — |
| | 12.5 | 3 | 5 | 5 | 2 | — |
| 83 | 25 | 5 | 5 | 5 | 5 | + |
| | 12.5 | 5 | 5 | 5 | 4 | — |
| | 6.25 | 4 | 5 | 5 | 3 | — |
| 84 | 25 | 5 | 5 | 5 | 5 | ± |
| | 12.5 | 5 | 5 | 5 | 4.5 | — |
| | 6.25 | 4.5 | 5 | 5 | 3 | — |
| 85 | 25 | 5 | 5 | 5 | 3 | — |
| | 12.5 | 5 | 5 | 5 | 2 | — |
| | 6.25 | 5 | 5 | 5 | 2 | — |
| 86 | 25 | 5 | 5 | 5 | 3 | — |
| | 12.5 | 5 | 5 | 5 | 2 | — |
| 87 | 25 | 5 | 5 | 5 | 3 | — |
| | 12.5 | 5 | 5 | 5 | 2 | — |
| 88 | 25 | 5 | 5 | 5 | 5 | ± |
| | 12.5 | 5 | 5 | 5 | 5 | — |
| | 6.25 | 5 | 5 | 5 | 4 | — |
| 89 | 25 | 5 | 5 | 5 | 5 | + |
| | 12.5 | 5 | 5 | 5 | 5 | ± |
| | 6.25 | 5 | 5 | 5 | 5 | — |
| 90 | 25 | 5 | 5 | 5 | 5 | + |
| | 12.5 | 5 | 5 | 5 | 5 | ± |
| | 6.25 | 5 | 5 | 5 | 5 | — |
| 91 | 25 | 5 | 5 | 5 | 5 | ± |
| | 12.5 | 5 | 5 | 5 | 5 | — |
| | 6.25 | 5 | 5 | 5 | 5 | — |
| 92 | 25 | 5 | 5 | 5 | 5 | + |
| | 12.5 | 5 | 5 | 5 | 5 | ± |

TABLE 3-continued

Test Example 1: Pre-emergence treatment under flooded condition

| Compound No. | Dosage g/a | Barnyard grass | Broad leaf (1) | Umbrella plant | Arrowheed | Phytotoxicity against paddy rice |
|---|---|---|---|---|---|---|
| | 6.25 | 5 | 5 | 5 | 5 | — |
| 93 | 25 | 5 | 5 | 5 | 5 | ± |
| | 12.5 | 5 | 5 | 5 | 5 | ± |
| | 6.25 | 5 | 5 | 5 | 4.5 | — |
| 94 | 25 | 5 | 5 | 5 | 5 | ± |
| | 12.5 | 5 | 5 | 5 | 5 | ± |
| | 6.25 | 5 | 5 | 5 | 4.5 | — |
| 95 | 25 | 5 | 5 | 5 | 5 | ± |
| | 12.5 | 5 | 5 | 5 | 5 | — |
| | 6.25 | 5 | 5 | 5 | 4.5 | — |
| 96 | 25 | 5 | 5 | 5 | 5 | ± |
| | 12.5 | 5 | 5 | 5 | 4.5 | — |
| | 6.25 | 5 | 5 | 5 | 4 | — |
| 97 | 25 | 5 | 5 | 5 | 5 | + |
| | 12.5 | 5 | 5 | 5 | 5 | ± |
| | 6.25 | 5 | 5 | 5 | 5 | ± |
| 98 | 25 | 5 | 5 | 5 | 5 | ± |
| | 12.5 | 5 | 5 | 5 | 4.5 | — |
| | 6.25 | 5 | 5 | 5 | 4 | — |
| 99 | 25 | 5 | 5 | 5 | 5 | ± |
| | 12.5 | 5 | 5 | 5 | 4.5 | — |
| | 6.25 | 5 | 5 | 5 | 4 | — |
| 100 | 25 | 5 | 5 | 5 | 5 | ± |
| | 12.5 | 5 | 5 | 5 | 5 | ± |
| | 6.25 | 5 | 5 | 5 | 4.5 | — |
| 101 | 25 | 5 | 5 | 5 | 5 | — |
| | 12.5 | 5 | 5 | 5 | 4.5 | — |
| | 6.25 | 5 | 5 | 5 | 4 | — |
| 102 | 25 | 5 | 5 | 5 | 5 | ± |
| | 12.5 | 5 | 5 | 5 | 4.5 | — |
| | 6.25 | 5 | 5 | 5 | 4.5 | — |
| 103 | 25 | 5 | 5 | 5 | 5 | ± |
| | 12.5 | 5 | 5 | 5 | 5 | — |
| | 6.25 | 5 | 5 | 5 | 5 | — |
| 104 | 25 | 5 | 5 | 5 | 5 | ± |
| | 12.5 | 5 | 5 | 5 | 5 | — |
| | 6.25 | 5 | 5 | 5 | 5 | — |
| 104 | 25 | 5 | 5 | 5 | 5 | ± |
| | 12.5 | 5 | 5 | 5 | 5 | — |
| | 6.25 | 5 | 5 | 5 | 5 | — |
| 105 | 25 | 5 | 5 | 5 | 5 | ± |
| | 12.5 | 5 | 5 | 5 | 5 | — |
| | 6.25 | 5 | 5 | 5 | 5 | — |
| 106 | 25 | 5 | 5 | 5 | 5 | — |
| | 12.5 | 5 | 5 | 5 | 5 | — |
| | 6.25 | 5 | 5 | 5 | 5 | — |
| 107 | 25 | 5 | 5 | 5 | 5 | ± |
| | 12.5 | 5 | 5 | 5 | 5 | — |
| | 6.25 | 5 | 5 | 5 | 5 | — |
| 108 | 25 | 5 | 5 | 5 | 5 | + |
| | 12.5 | 5 | 5 | 5 | 5 | ± |
| | 6.25 | 5 | 5 | 5 | 5 | ± |
| 109 | 25 | 5 | 5 | 5 | 5 | + |
| | 12.5 | 5 | 5 | 5 | 5 | ± |
| | 6.25 | 5 | 5 | 5 | 5 | ± |
| 110 | 25 | 5 | 5 | 5 | 5 | — |
| | 12.5 | 5 | 5 | 5 | 5 | — |
| | 6.25 | 5 | 5 | 5 | 5 | — |
| 111 | 25 | 5 | 5 | 5 | 5 | + |
| | 12.5 | 5 | 5 | 5 | 5 | ± |
| | 6.25 | 5 | 5 | 5 | 5 | — |
| 112 | 25 | 5 | 5 | 5 | 3 | — |
| | 12.5 | 4.8 | 5 | 5 | 3 | — |
| | 6.25 | 4.8 | 5 | 5 | 3 | — |
| 113 | 25 | 5 | 5 | 5 | 5 | + |
| | 12.5 | 5 | 5 | 5 | 5 | ± |
| | 6.25 | 5 | 5 | 5 | 5 | ± |
| 114 | 25 | 5 | 5 | 5 | 5 | + |
| | 12.5 | 5 | 5 | 5 | 5 | ± |
| | 6.25 | 5 | 5 | 5 | 5 | ± |
| 115 | 25 | 5 | 5 | 5 | 5 | + |
| | 12.5 | 5 | 5 | 5 | 5 | ± |
| | 6.25 | 5 | 5 | 5 | 5 | — |
| 116 | 25 | 5 | 5 | 5 | 5 | + |
| | 12.5 | 5 | 5 | 5 | 5 | ± |
| | 6.25 | 5 | 5 | 5 | 5 | ± |
| 117 | 25 | 5 | 5 | 5 | 5 | + |
| | 12.5 | 4.8 | 5 | 5 | 5 | ± |
| | 6.25 | 4.5 | 5 | 5 | 5 | ± |
| 118 | 25 | 5 | 5 | 5 | 5 | + |
| | 12.5 | 5 | 5 | 5 | 5 | ± |
| | 6.25 | 5 | 5 | 5 | 4 | ± |
| 128 | 25 | 5 | 5 | 5 | 4 | + |
| | 12.5 | 4.5 | 5 | 5 | 3 | ± |
| | 6.25 | 4 | 5 | 5 | 2 | — |
| 131 | 25 | 5 | 5 | 5 | 4 | ± |
| | 12.5 | 5 | 5 | 5 | 3 | — |
| | 6.25 | 5 | 5 | 5 | 1 | — |
| 133 | 25 | 5 | 5 | 5 | 5 | — |
| | 12.5 | 4 | 5 | 5 | 4 | — |
| | 6.25 | 3 | 5 | 5 | 3 | — |
| 134 | 25 | 5 | 5 | 5 | 4 | ± |
| | 12.5 | 5 | 5 | 5 | 2 | — |
| | 6.25 | 4 | 5 | 5 | 1 | — |
| 138 | 25 | 5 | 5 | 5 | 4 | — |
| | 12.5 | 5 | 5 | 5 | 3 | — |
| | 6.25 | 4 | 5 | 5 | 2 | — |
| 139 | 25 | 5 | 5 | 5 | 5 | — |
| | 12.5 | 5 | 5 | 5 | 4 | — |
| | 6.25 | 4.5 | 5 | 5 | 3 | — |
| 140 | 25 | 5 | 5 | 5 | 4 | — |
| | 12.5 | 4 | 5 | 5 | 3 | — |
| | 6.25 | 3 | 4 | 4 | 2 | — |
| 146 | 25 | 5 | 5 | 5 | 5 | + |
| | 12.5 | 5 | 5 | 5 | 5 | ± |
| | 6.25 | 5 | 5 | 5 | 5 | — |
| 147 | 25 | 5 | 5 | 5 | 5 | ± |
| | 12.5 | 5 | 5 | 5 | 5 | — |
| | 6.25 | 5 | 5 | 5 | 5 | — |
| 148 | 25 | 5 | 5 | 5 | 5 | ± |
| | 12.5 | 5 | 5 | 5 | 5 | — |
| | 6.25 | 5 | 5 | 5 | 5 | — |
| 150 | 25 | 5 | 5 | 5 | 4 | — |
| | 12.5 | 5 | 5 | 5 | 3 | — |
| | 6.25 | 4 | 4 | 4 | 1 | — |
| 151 | 25 | 5 | 5 | 5 | 3 | — |
| | 12.5 | 5 | 5 | 5 | 1 | — |
| | 6.25 | 4.5 | 5 | 5 | 0.5 | — |
| 157 | 25 | 5 | 5 | 5 | 5 | + |
| | 12.5 | 5 | 5 | 5 | 5 | ± |
| | 6.25 | 5 | 5 | 5 | 5 | — |
| 160 | 25 | 5 | 5 | 5 | 5 | — |
| | 12.5 | 5 | 5 | 5 | 5 | — |
| | 6.25 | 4.5 | 5 | 5 | 5 | — |
| 162 | 25 | 5 | 5 | 5 | 5 | — |
| | 12.5 | 5 | 5 | 5 | 5 | — |
| | 6.25 | 5 | 5 | 5 | 4 | — |
| 171 | 25 | 5 | 5 | 5 | 5 | — |
| | 12.5 | 5 | 5 | 5 | 4.5 | — |
| | 6.25 | 5 | 5 | 5 | 3 | — |
| 177 | 25 | 5 | 5 | 5 | 4 | — |
| | 12.5 | 5 | 5 | 5 | 3 | ± |
| | 6.25 | 4 | 5 | 5 | 1 | — |
| 180 | 25 | 5 | 5 | 5 | 5 | + |
| | 12.5 | 5 | 5 | 5 | 5 | ± |
| | 6.25 | 5 | 5 | 5 | 5 | — |
| 169 | 25 | 5 | 5 | 5 | 4.5 | — |
| | 12.5 | 5 | 5 | 5 | 2 | — |
| | 6.25 | 3 | 5 | 5 | 1 | — |
| 170 | 25 | 5 | 5 | 5 | 5 | + |
| | 12.5 | 5 | 5 | 5 | 5 | — |
| | 6.25 | 5 | 5 | 5 | 4 | — |
| Known compound No. 2 | 25 | 5 | 5 | 5 | 2 | + |
| | 12.5 | 4.5 | 5 | 5 | 0.5 | ± |
| | 6.25 | 1 | 5 | 5 | 0 | — |
| Known compound No. 1 | 50 | 0 | 0 | 0 | 0 | — |
| | 25 | 0 | 0 | 0 | 0 | — |

TABLE 3-continued

Test Example 1: Pre-emergence treatment under flooded condition

| Compound No. | Dosage g/a | Herbicidal activity | | | | Phytotoxicity against paddy rice |
|---|---|---|---|---|---|---|
| | | Barnyard grass | Broad leaf (1) | Umbrella plant | Arrowheed | |
| Standard compound A | 25 | 3 | 4 | 3 | 0 | + |
| | 12.5 | 1 | 2 | 0 | 0 | — |

Remarks: (1) Broad leaf: Mixture of barnyard grass, toothcup, false pinpernel, water wort
Known compound No. 1

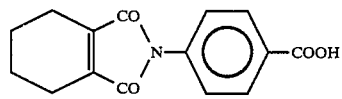

Standard compound A

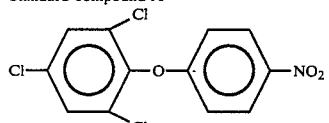

Known compound No. 2

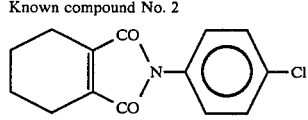

Test Example 2: Post-emergence treatment in flooded condition

A fixed amount of paddy field soil was filled in each Wagner pot sized 1/5,000 are to provide a condition similar to a paddy field and there was sown a fixed amount of seeds of barnyard grass, monochoria, toothcup, false pimpernel, water wort and umbrella plant.

In addition tubers of arrowhead were buried 1 cm under the surface of soil at the rate of 3 pieces per pot, three 2.5-leaf stage rice seedlings (variety: Nihonbare) were transplanted from a nursery, the pot was flooded with water 3 cm deep and then placed in a greenhouse.

When the weeds grew to reach 2 to 3-leaf stage, a diluted solution of the compound of the present invention, was applied to the flood at a rate of 12.5 to 50 g of the compound of the present invention per are.

After 30 days from the treatment with the diluted solution, the herbicidal activity was observed and obtained the results as shown in Table 4. The classification basis of the results is the same with Test Example 1.

TABLE 4

Test Example 2: Post-emergence treatment in flooded condition

| Compound No. | Dosage g/a | Herbicidal activity | | | |
|---|---|---|---|---|---|
| | | Barnyard grass | broad leaf (1) | Umbrella plant | Arrowheed |
| 3 | 25 | 5 | 5 | 5 | 5 |
| | 12.5 | 5 | 5 | 5 | 4.5 |
| 5 | 25 | 5 | 5 | 5 | 4.5 |
| | 12.5 | 5 | 5 | 5 | 3 |
| 7 | 25 | 5 | 5 | 5 | 4 |
| | 12.5 | 5 | 5 | 5 | 3 |
| 9 | 50 | 5 | 5 | 5 | 3 |
| | 25 | 5 | 5 | 5 | 2 |
| 10 | 25 | 5 | 5 | 5 | 4 |
| | 12.5 | 5 | 5 | 5 | 3 |
| 11 | 25 | 5 | 5 | 5 | 3.5 |
| | 12.5 | 4 | 5 | 5 | 2.5 |
| 12 | 50 | 4.5 | 5 | 5 | 4 |
| | 25 | 4 | 5 | 5 | 3 |
| 13 | 25 | 5 | 5 | 5 | 4.5 |
| | 12.5 | 5 | 5 | 5 | 3 |
| 14 | 50 | 5 | 5 | 5 | 3 |
| | 25 | 4.5 | 5 | 5 | 2 |
| 15 | 50 | 4 | 5 | 5 | 3.5 |
| | 25 | 3 | 5 | 5 | 2 |
| 23 | 50 | 4.5 | 5 | 5 | 5 |
| | 25 | 3 | 5 | 5 | 3.5 |
| 26 | 25 | 5 | 5 | 5 | 5 |
| | 12.5 | 5 | 5 | 5 | 3.5 |
| 27 | 25 | 5 | 5 | 5 | 5 |
| | 12.5 | 5 | 5 | 5 | 4.5 |
| 28 | 25 | 5 | 5 | 5 | 4.5 |
| | 12.5 | 5 | 5 | 5 | 3 |
| 29 | 25 | 5 | 5 | 5 | 5 |
| | 12.5 | 5 | 5 | 5 | 5 |
| 30 | 25 | 5 | 5 | 5 | 5 |
| | 12.5 | 5 | 5 | 5 | 5 |
| 31 | 25 | 4.5 | 5 | 5 | 5 |
| | 12.5 | 3 | 5 | 5 | 3 |
| 32 | 50 | 5 | 5 | 5 | 5 |
| | 25 | 5 | 5 | 5 | 4.5 |
| 33 | 50 | 5 | 5 | 5 | 4.5 |
| | 25 | 4.5 | 5 | 5 | 4 |
| 34 | 50 | 4 | 5 | 5 | 4 |
| | 25 | 3 | 5 | 5 | 3 |
| 35 | 50 | 3 | 5 | 5 | 4.5 |
| | 25 | 2 | 5 | 5 | 3 |
| 36 | 50 | 3 | 5 | 5 | 3 |
| | 25 | 2 | 5 | 5 | 2 |
| 39 | 25 | 4 | 5 | 5 | 3 |
| | 12.5 | 3 | 5 | 5 | 2 |
| 40 | 25 | 5 | 5 | 5 | 5 |
| | 12.5 | 4 | 5 | 5 | 3 |
| 42 | 25 | 4 | 5 | 5 | 4 |
| | 12.5 | 3 | 5 | 5 | 3 |
| 43 | 50 | 3 | 5 | 5 | 3.5 |
| | 25 | 2 | 5 | 5 | 3 |
| 45 | 25 | 4.5 | 5 | 5 | 3 |
| | 12.5 | 3 | 5 | 5 | 2 |
| 47 | 25 | 5 | 5 | 5 | 5 |
| | 12.5 | 5 | 5 | 5 | 5 |
| 48 | 25 | 5 | 5 | 5 | 5 |
| | 12.5 | 5 | 5 | 5 | 3 |
| 49 | 25 | 5 | 5 | 5 | 3 |
| | 12.5 | 3 | 5 | 5 | 2 |
| 55 | 50 | 3 | 5 | 5 | 5 |
| | 25 | 2 | 5 | 5 | 5 |
| 56 | 25 | 5 | 5 | 5 | 5 |
| | 12.5 | 5 | 5 | 5 | 5 |
| 58 | 50 | 3 | 5 | 5 | 3 |
| | 25 | 2 | 5 | 5 | 2 |
| 62 | 50 | 3 | 5 | 5 | 3 |
| | 25 | 2 | 5 | 5 | 2 |
| 63 | 25 | 5 | 5 | 5 | 5 |
| | 12.5 | 5 | 5 | 5 | 5 |
| 64 | 25 | 5 | 5 | 5 | 5 |
| | 12.5 | 5 | 5 | 5 | 5 |
| 65 | 25 | 5 | 5 | 5 | 5 |
| | 12.5 | 5 | 5 | 5 | 5 |
| 66 | 25 | 5 | 5 | 5 | 5 |
| | 12.5 | 5 | 5 | 5 | 5 |
| 67 | 50 | 3 | 5 | 5 | 5 |
| | 25 | 2 | 5 | 5 | 5 |
| 73 | 50 | 3 | 5 | 5 | 3 |
| | 25 | 2 | 5 | 5 | 2 |
| 76 | 50 | 4 | 5 | 5 | 4 |
| | 25 | 3 | 5 | 5 | 3 |
| 77 | 50 | 4 | 5 | 5 | 3.5 |
| | 25 | 2 | 5 | 5 | 2 |
| 78 | 50 | 3 | 5 | 5 | 3.5 |
| | 25 | 2 | 5 | 5 | 2 |
| 83 | 50 | 5 | 5 | 5 | 3 |

TABLE 4-continued

Test Example 2:
Post-emergence treatment in flooded condition

| Compound No. | Dosage g/a | Barnyard grass | broad leaf (1) | Umbrella plant | Arrowheed |
|---|---|---|---|---|---|
| | 25 | 4.5 | 5 | 5 | 2 |
| 84 | 25 | 4 | 5 | 5 | 4.5 |
| | 12.5 | 2 | 5 | 5 | 3 |
| 86 | 50 | 3 | 5 | 5 | 3 |
| | 25 | 2 | 5 | 5 | 2 |
| 89 | 25 | 5 | 5 | 5 | 5 |
| | 12.5 | 4 | 5 | 5 | 5 |
| | 6.25 | 3 | 5 | 5 | 5 |
| 90 | 25 | 5 | 5 | 5 | 5 |
| | 12.5 | 5 | 5 | 5 | 5 |
| | 6.25 | 5 | 5 | 5 | 5 |
| 91 | 25 | 5 | 5 | 5 | 5 |
| | 12.5 | 5 | 5 | 5 | 5 |
| | 6.25 | 5 | 5 | 5 | 5 |
| 92 | 25 | 5 | 5 | 5 | 5 |
| | 12.5 | 5 | 5 | 5 | 5 |
| | 6.25 | 5 | 5 | 5 | 5 |
| 93 | 25 | 5 | 5 | 5 | 5 |
| | 12.5 | 5 | 5 | 5 | 5 |
| | 6.25 | 5 | 5 | 5 | 4 |
| 94 | 25 | 5 | 5 | 5 | 5 |
| | 12.5 | 5 | 5 | 5 | 4.5 |
| | 6.25 | 5 | 5 | 5 | 4 |
| 95 | 25 | 5 | 5 | 5 | 5 |
| | 12.5 | 5 | 5 | 5 | 4.5 |
| | 6.25 | 5 | 5 | 5 | 4.5 |
| 96 | 25 | 5 | 5 | 5 | 5 |
| | 12.5 | 5 | 5 | 5 | 4 |
| | 6.25 | 4 | 5 | 5 | 3 |
| 97 | 25 | 5 | 5 | 5 | 5 |
| | 12.5 | 5 | 5 | 5 | 5 |
| | 6.25 | 5 | 5 | 5 | 5 |
| 98 | 25 | 5 | 5 | 5 | 5 |
| | 12.5 | 5 | 5 | 5 | 4.5 |
| | 6.25 | 5 | 5 | 5 | 4 |
| 99 | 25 | 5 | 5 | 5 | 5 |
| | 12.5 | 5 | 5 | 5 | 4.5 |
| | 6.25 | 5 | 5 | 5 | 4 |
| 100 | 25 | 5 | 5 | 5 | 5 |
| | 12.5 | 5 | 5 | 5 | 4.5 |
| | 6.25 | 5 | 5 | 5 | 4 |
| 101 | 25 | 5 | 5 | 5 | 5 |
| | 12.5 | 5 | 5 | 5 | 4 |
| | 6.25 | 5 | 5 | 5 | 3 |
| 102 | 25 | 5 | 5 | 5 | 5 |
| | 12.5 | 5 | 5 | 5 | 4.5 |
| | 6.25 | 5 | 5 | 5 | 4 |
| 103 | 25 | 5 | 5 | 5 | 5 |
| | 12.5 | 5 | 5 | 5 | 5 |
| | 6.25 | 5 | 5 | 5 | 5 |
| 104 | 25 | 5 | 5 | 5 | 5 |
| | 12.5 | 5 | 5 | 5 | 5 |
| | 6.25 | 5 | 5 | 5 | 5 |
| 106 | 25 | 5 | 5 | 5 | 5 |
| | 12.5 | 5 | 5 | 5 | 5 |
| | 6.25 | 5 | 5 | 5 | 5 |
| 126 | 50 | 5 | 5 | 5 | 5 |
| | 25 | 2 | 4.5 | 5 | 2 |
| 127 | 50 | 4 | 5 | 5 | 5 |
| | 25 | 2 | 5 | 5 | 2.5 |
| 145 | 50 | 4.5 | 5 | 5 | 4 |
| | 25 | 2 | 5 | 5 | 3 |
| 146 | 50 | 5 | 5 | 5 | 5 |
| | 25 | 5 | 5 | 5 | 2.5 |
| 177 | 50 | 5 | 5 | 5 | 5 |
| | 25 | 4.5 | 5 | 5 | 4 |
| 179 | 50 | 4 | 5 | 5 | 5 |
| | 25 | 3 | 4 | 5 | 2.5 |
| 181 | 50 | 5 | 5 | 5 | 5 |
| | 25 | 4 | 4.5 | 5 | 3 |
| 168 | 50 | 4 | 5 | 5 | 5 |
| | 25 | 3 | 5 | 5 | 3 |
| 169 | 50 | 5 | 5 | 5 | 5 |
| | 25 | 3 | 5 | 5 | 3 |
| Known compound No. 1 | 50 | 0 | 0 | 0 | 0 |
| | 25 | 0 | 0 | 0 | 0 |
| Known compound No. 2 | 50 | 3.5 | 5 | 5 | 5 |
| | 25 | 0.5 | 4.5 | 5 | 0.5 |
| Standard compound A | 50 | 1 | 1 | 0 | 0 |
| | 25 | 0 | 0 | 0 | 0 |

Test Example 3: Test on perennial weeds in a paddy field

Wagner pots sized 1/5,000 are were filled with a fixed amount of paddy field soil to provide a condition similar to a paddy field and there was sown a fixed amount of seeds of bulrush. In addition tubers of mizugayatsuri and water chestnut were buried 3 cm under the surface of soil at the rate of 3 pieces per pot and then the pot was flooded with water 3 cm deep.

The pre-emergence treatment was conducted on the second day after seeds and tubers of the weeds were put into soil, while the post-emergence treatment was effected at 2-leaf stage of bulrush, 2 to 3-leaf stage of mizugayatsuri and the time when water chestnut grew 5 to 6 cm high, at each time a diluted solution of the compound of the present invention was applied to the flood at a rate of 6.25 to 50 g of the compound of the present invention per are.

The herbicidal activity was observed on 30th day after each treatment and the test results are shown in Table 5. The judging standard of the results is the same with Test Example 1.

TABLE 5

Test Example 3:
Test on perennial weeds in paddy field

| Compound No. | Dosage g/a | Pre-emergence treatment | | | Post-emergence treatment | | |
|---|---|---|---|---|---|---|---|
| | | Bulrush | Mizugayatsuri | Water chestnut | Bulrush | Mizugayatsuri | Water chestnut |
| 3 | 50 | 5 | 5 | 4 | 5 | 4 | 3.5 |
| | 25 | 5 | 4 | 3 | 5 | 3.5 | 2.5 |
| | 12.5 | 5 | 3 | 2.5 | 5 | 3 | 2 |
| 5 | 25 | 5 | 5 | 5 | 5 | 3 | 2.5 |
| | 12.5 | 5 | 5 | 5 | 5 | 3 | 2 |
| | 6.25 | 5 | 5 | 5 | 5 | 2.5 | 2 |
| 7 | 25 | 5 | 5 | 5 | 5 | 5 | 4 |
| | 12.5 | 5 | 5 | 5 | 5 | 4.5 | 3 |
| | 6.25 | 5 | 5 | 5 | 5 | 4 | 2 |
| 11 | 50 | 5 | 4.5 | 4 | 5 | 4 | 2.5 |
| | 25 | 4 | 3 | 3 | 4 | 3 | 2 |
| | 12.5 | 3 | 2.5 | 2 | 3 | 2 | 2 |
| 13 | 50 | 5 | 5 | 4 | 5 | 4.5 | 3.5 |
| | 25 | 4 | 5 | 2.5 | 4 | 3 | 3 |
| | 12.5 | 3 | 3 | 2 | 3 | 2 | 2 |
| 14 | 25 | 5 | 4 | 4 | 5 | 4 | 3.5 |
| | 12.5 | 5 | 3 | 2.5 | 4 | 3 | 2.5 |
| | 6.25 | 5 | 2 | 2 | 3 | 2 | 2 |
| 28 | 25 | 5 | 5 | 5 | 5 | 5 | 5 |
| | 12.5 | 5 | 5 | 5 | 5 | 5 | 5 |
| | 6.25 | 5 | 5 | 5 | 5 | 5 | 4.5 |
| 29 | 25 | 5 | 5 | 5 | 5 | 5 | 4 |
| | 12.5 | 5 | 5 | 5 | 3 | 4.5 | 3 |
| | 6.25 | 5 | 5 | 5 | 2 | 2 | 2 |
| 31 | 50 | 5 | 5 | 4 | 5 | 5 | 3 |
| | 25 | 4 | 5 | 3 | 4 | 4.5 | 2 |

TABLE 5-continued

Test Example 3: Test on perennial weeds in paddy field

| Compound No. | Dosage g/a | Pre-emergence treatment | | | Post-emergence treatment | | |
|---|---|---|---|---|---|---|---|
| | | Bulrush | Mizugayatsuri | Water chestnut | Bulrush | Mizugayatsuri | Water chestnut |
| | 12.5 | 3 | 5 | 2 | 2.5 | 4 | 2 |
| 32 | 25 | 5 | 5 | 4 | 4.5 | 4 | 3 |
| | 12.5 | 5 | 5 | 3 | 3.5 | 3 | 2.5 |
| | 6.25 | 5 | 5 | 2 | 2 | 2 | 2 |
| 33 | 50 | 5 | 5 | 4 | 5 | 5 | 3.5 |
| | 25 | 4 | 5 | 3 | 3.5 | 4 | 2 |
| | 12.5 | 2.5 | 5 | 2.5 | 2 | 3 | 2 |
| 34 | 25 | 5 | 5 | 4.5 | 4 | 4.5 | 3 |
| | 12.5 | 5 | 5 | 3 | 3 | 3 | 2.5 |
| | 6.25 | 5 | 5 | 2 | 2 | 2 | 2 |
| 39 | 25 | 5 | 5 | 5 | 5 | 5 | 4 |
| | 12.5 | 5 | 5 | 3 | 4 | 3.5 | 3 |
| | 6.25 | 5 | 3 | 2 | 3 | 3 | 2 |
| 44 | 25 | 5 | 5 | 5 | 3.5 | 3 | 2.5 |
| | 12.5 | 5 | 4.5 | 3 | 3 | 2.5 | 2 |
| | 6.25 | 4.5 | 4 | 2 | 2 | 2 | 2 |
| 63 | 25 | 5 | 5 | 5 | 5 | 5 | 4.5 |
| | 12.5 | 5 | 5 | 4.5 | 5 | 4.5 | 4 |
| | 6.25 | 5 | 5 | 4 | 5 | 4 | 4 |
| 64 | 25 | 5 | 5 | 5 | 5 | 5 | 5 |
| | 12.5 | 5 | 5 | 5 | 5 | 5 | 4.5 |
| | 6.25 | 5 | 5 | 4 | 5 | 4.5 | 4 |
| 65 | 25 | 5 | 5 | 5 | 5 | 5 | 4 |
| | 12.5 | 5 | 5 | 5 | 5 | 4.5 | 3.5 |
| | 6.25 | 5 | 5 | 4 | 5 | 4 | 3 |
| 66 | 25 | 5 | 5 | 4.5 | 5 | 4.5 | 4 |
| | 12.5 | 5 | 4.5 | 4 | 4 | 3 | 3 |
| | 6.25 | 5 | 4 | 4 | 3 | 2 | 2 |
| 67 | 50 | 5 | 5 | 4.5 | 5 | 4 | 3.5 |
| | 25 | 5 | 4 | 4 | 4 | 3 | 3 |
| | 12.5 | 5 | 3 | 3 | 3 | 2 | 2 |
| 84 | 25 | 5 | 4 | 4 | 5 | 4.5 | 3.5 |
| | 12.5 | 5 | 4 | 3 | 4 | 3.5 | 2.5 |
| | 6.25 | 4.5 | 3 | 2 | 3 | 2.5 | 2 |
| 89 | 25 | 5 | 5 | 5 | 5 | 5 | 5 |
| | 12.5 | 5 | 5 | 4.5 | 4.5 | 5 | 4 |
| | 6.25 | 5 | 4 | 4 | 4 | 4 | 3 |
| 90 | 25 | 5 | 5 | 5 | 5 | 5 | 5 |
| | 12.5 | 5 | 5 | 5 | 4.5 | 4.5 | 4 |
| | 6.25 | 5 | 5 | 4 | 4 | 4.5 | 3 |
| 91 | 25 | 5 | 5 | 4.5 | 5 | 5 | 5 |
| | 12.5 | 5 | 5 | 4 | 4 | 5 | 4.5 |
| | 6.25 | 5 | 5 | 3.5 | 3 | 4.5 | 3 |
| 92 | 25 | 5 | 5 | 5 | 5 | 5 | 4.5 |
| | 12.5 | 5 | 5 | 5 | 4.5 | 5 | 4 |
| | 6.25 | 5 | 5 | 5 | 4 | 4.5 | 4 |
| 93 | 25 | 5 | 5 | 5 | 5 | 5 | 5 |
| | 12.5 | 5 | 5 | 5 | 5 | 5 | 4 |
| | 6.25 | 5 | 5 | 5 | 5 | 4.5 | 3 |
| 94 | 25 | 5 | 5 | 5 | 5 | 5 | 4.5 |
| | 12.5 | 5 | 5 | 4.5 | 5 | 4.5 | 4.5 |
| | 6.25 | 5 | 5 | 5 | 4.5 | 5 | 4 |
| 95 | 25 | 5 | 5 | 5 | 5 | 5 | 4 |
| | 12.5 | 5 | 4.5 | 4 | 4.5 | 4 | 3 |
| | 6.25 | 5 | 4.5 | 4 | 4 | 3.5 | 2.5 |
| 96 | 25 | 5 | 5 | 5 | 5 | 5 | 5 |
| | 12.5 | 5 | 5 | 4.5 | 4.5 | 4.5 | 4 |
| | 6.25 | 5 | 5 | 4.5 | 4 | 4 | 3 |
| 97 | 25 | 5 | 5 | 5 | 5 | 5 | 4 |
| | 12.5 | 5 | 5 | 4.5 | 5 | 5 | 3 |
| | 6.25 | 5 | 4.5 | 4 | 4 | 4.5 | 2 |
| 98 | 25 | 5 | 5 | 5 | 5 | 5 | 4.5 |
| | 12.5 | 5 | 5 | 4.5 | 5 | 5 | 4 |
| | 6.25 | 5 | 5 | 4.5 | 4 | 5 | 3 |
| 99 | 25 | 5 | 5 | 5 | 5 | 5 | 5 |
| | 12.5 | 5 | 5 | 5 | 5 | 5 | 4 |
| | 6.25 | 5 | 5 | 4.5 | 4.5 | 5 | 3 |
| 100 | 25 | 5 | 5 | 4.5 | 5 | 5 | 4 |
| | 12.5 | 5 | 4.5 | 4.5 | 5 | 4.5 | 3 |
| | 6.25 | 5 | 4.5 | 4 | 4.5 | 4 | 2.5 |
| 101 | 25 | 5 | 5 | 5 | 5 | 5 | 4.5 |
| | 12.5 | 5 | 4.5 | 4 | 4.5 | 4.5 | 4.5 |
| | 6.25 | 5 | 4.5 | 3 | 4.5 | 4 | 3 |
| 102 | 25 | 5 | 5 | 5 | 5 | 5 | 5 |
| | 12.5 | 5 | 5 | 4.5 | 5 | 5 | 4 |
| | 6.25 | 5 | 5 | 4.5 | 3 | 3 | 3 |
| 103 | 25 | 5 | 5 | 5 | 5 | 5 | 4 |
| | 12.5 | 5 | 5 | 5 | 4.5 | 4 | 3 |
| | 6.25 | 5 | 4.5 | 4.5 | 4 | 3 | 2.5 |
| 104 | 25 | 5 | 5 | 5 | 5 | 5 | 5 |
| | 12.5 | 5 | 5 | 4.5 | 5 | 5 | 4.5 |
| | 6.25 | 5 | 4.5 | 4.5 | 5 | 5 | 4.5 |
| 106 | 25 | 5 | 5 | 5 | 5 | 5 | 5 |
| | 12.5 | 5 | 5 | 5 | 5 | 4 | 4.5 |
| | 6.25 | 5 | 5 | 5 | 5 | 3.5 | 4.5 |
| 131 | 25 | 5 | 5 | 4.5 | 5 | 5 | 4 |
| | 12.5 | 5 | 4 | 3 | 5 | 4 | 3 |
| | 6.25 | 5 | 3 | 2 | 5 | 3 | 2 |
| 146 | 25 | 5 | 5 | 5 | 5 | 5 | 5 |
| | 12.5 | 5 | 4 | 5 | 5 | 4 | 5 |
| | 6.25 | 5 | 3 | 5 | 5 | 3 | 5 |
| 147 | 25 | 5 | 5 | 5 | 5 | 5 | 5 |
| | 12.5 | 5 | 5 | 5 | 5 | 5 | 5 |
| | 6.25 | 5 | 5 | 5 | 5 | 4 | 3 |
| 148 | 25 | 5 | 5 | 5 | 5 | 5 | 5 |
| | 12.5 | 5 | 5 | 5 | 5 | 5 | 5 |
| | 6.25 | 5 | 5 | 5 | 5 | 5 | 5 |
| 149 | 25 | 5 | 5 | 5 | 5 | 5 | 5 |
| | 12.5 | 5 | 4 | 5 | 5 | 4 | 5 |
| | 6.25 | 5 | 3 | 5 | 4 | 3 | 5 |
| 162 | 25 | 5 | 5 | 5 | 5 | 5 | 5 |
| | 12.5 | 5 | 4 | 3 | 5 | 4 | 3 |
| | 6.25 | 4 | 3 | 2 | 3 | 2 | 2 |
| 165 | 25 | 5 | 5 | 5 | 5 | 5 | 5 |
| | 12.5 | 5 | 4 | 3 | 4 | 5 | 4.5 |
| | 6.25 | 4 | 2 | 1 | 3 | 3 | 4 |
| 168 | 25 | 5 | 5 | 4 | 5 | 5 | 5 |
| | 12.5 | 5 | 4.5 | 3 | 5 | 5 | 5 |
| | 6.25 | 4.5 | 3 | 1 | 4 | 3 | 3 |
| Known compound No. 1 | 25 | 3 | 0 | 0 | 0 | 0 | 0 |
| | 12.5 | 2 | 0 | 0 | 0 | 0 | 0 |
| | 6.25 | 1 | 0 | 0 | 0 | 0 | 0 |
| Known compound No. 2 | 25 | 4 | 3 | 4 | 3 | 2 | 4.5 |
| | 12.5 | 2.5 | 2 | 2 | 2 | 1 | 2 |
| | 6.25 | 1 | 1 | 0 | 1 | 0 | 1 |
| Standard compound A | 50 | 2 | 0 | 0 | 0 | 0 | 0 |
| | 25 | 1 | 0 | 0 | 0 | 0 | 0 |
| | 12.5 | 0 | 0 | 0 | 0 | 0 | 0 |

As seen in the results of Test example 1, 2 and 3, the compounds of the present invention showed remarkable herbicidal effect against the principal annual and perennial weeds in paddy fields in pre- and post emergence treatment.

Furthermore, it was found that the compound of the present invention showed only little phytotoxicity in pre- and post transplantation treatment.

Then the Test examples in field are shown as follows.

Test Example 4: Pre-emergence soil surface treatment

A fixed amount of field soil was filled in a round plastic case 8 cm across and 8 cm deep, and a fixed amount of seeds of crabgrass, foxtail, pigweed, lamb's-quarters was sown followed by covering them with soil 0.5 to 1 cm thick. Then immediately a diluted solution of the compound of the present invention was applied to treat the whole surface of soil in case at a rate of 12.5 to 25 g of the compound of the present invention per are.

After the treatment the cultivation was done in a greenhouse and the herbicidal activity was observed on the 20th day. The test was carried out on 2-replication system and each average value was sought. The judging standard of the results is the same with Test Example 1. The test results are shown in Table 6.

TABLE 6

Test Example 4: Pre-emergence soil surface treatment

| Compound No. | Dosage g/a | Herbicidal effect | | | |
|---|---|---|---|---|---|
| | | foxtail | crabgrass | pigweed | buckwheat |
| 2 | 25 | 5 | 5 | 5 | 5 |
| | 12.5 | 4 | 5 | 5 | 5 |
| 3 | 25 | 5 | 5 | 5 | 5 |
| | 12.5 | 4.5 | 5 | 5 | 5 |
| 5 | 25 | 5 | 5 | 5 | 5 |
| | 12.5 | 5 | 5 | 5 | 5 |
| 6 | 25 | 4.5 | 5 | 5 | 5 |
| | 12.5 | 4 | 4.5 | 5 | 4.5 |
| 7 | 25 | 5 | 5 | 5 | 5 |
| | 12.5 | 4.5 | 5 | 5 | 5 |
| 8 | 25 | 5 | 5 | 5 | 5 |
| | 12.5 | 5 | 5 | 5 | 5 |
| 9 | 25 | 4.5 | 5 | 5 | 5 |
| | 12.5 | 4 | 4.5 | 5 | 5 |
| 10 | 25 | 4.5 | 5 | 5 | 5 |
| | 12.5 | 4 | 5 | 5 | 5 |
| 11 | 25 | 4.5 | 5 | 5 | 5 |
| | 12.5 | 4 | 5 | 5 | 5 |
| 13 | 25 | 4.5 | 5 | 5 | 4.5 |
| | 12.5 | 4 | 4.5 | 5 | 4 |
| 14 | 25 | 4.5 | 4.5 | 5 | 5 |
| | 12.5 | 4 | 4 | 5 | 5 |
| 18 | 25 | 3 | 4 | 5 | 4 |
| | 12.5 | 2 | 3 | 5 | 3 |
| 27 | 25 | 4.5 | 5 | 5 | 5 |
| | 12.5 | 4.5 | 4.5 | 5 | 5 |
| 28 | 25 | 4 | 5 | 5 | 5 |
| | 12.5 | 3.5 | 4.5 | 5 | 4 |
| 29 | 25 | 4 | 4.5 | 5 | 5 |
| | 12.5 | 3 | 4 | 5 | 4 |
| 30 | 25 | 4 | 4.5 | 5 | 4.5 |
| | 12.5 | 3 | 4 | 5 | 4 |
| 31 | 25 | 3 | 4 | 5 | 4 |
| | 12.5 | 2 | 3 | 5 | 3 |
| 33 | 25 | 3 | 4 | 5 | 4 |
| | 12.5 | 2 | 3 | 5 | 3 |
| 34 | 25 | 3.5 | 4.5 | 5 | 4 |
| | 12.5 | 3 | 4 | 5 | 3 |
| 40 | 25 | 4 | 5 | 5 | 4.5 |
| | 12.5 | 3 | 4.5 | 5 | 3 |
| 41 | 25 | 5 | 5 | 5 | 5 |
| | 12.5 | 5 | 5 | 5 | 5 |
| 42 | 25 | 5 | 5 | 5 | 5 |
| | 12.5 | 5 | 5 | 5 | 5 |
| 43 | 25 | 4.5 | 4.5 | 5 | 5 |
| | 12.5 | 3 | 4 | 5 | 4 |
| 44 | 25 | 4 | 4.5 | 5 | 4.5 |
| | 12.5 | 3 | 4 | 5 | 4 |
| 48 | 25 | 4 | 4.5 | 5 | 5 |
| | 12.5 | 4 | 4 | 5 | 5 |
| 49 | 25 | 4 | 4 | 5 | 5 |
| | 12.5 | 3.5 | 3.5 | 5 | 4 |
| 63 | 25 | 5 | 5 | 5 | 5 |
| | 12.5 | 4.5 | 5 | 5 | 5 |
| 64 | 25 | 5 | 5 | 5 | 5 |
| | 12.5 | 5 | 5 | 5 | 5 |
| 65 | 25 | 5 | 5 | 5 | 5 |
| | 12.5 | 5 | 5 | 5 | 5 |
| 74 | 25 | 4 | 4 | 5 | 5 |
| | 12.5 | 3 | 3 | 5 | 4 |
| 80 | 25 | 3 | 4 | 5 | 5 |
| | 12.5 | 2 | 3 | 5 | 5 |
| 83 | 25 | 4.5 | 5 | 5 | 5 |
| | 12.5 | 4 | 5 | 5 | 5 |
| 84 | 25 | 4.5 | 4.5 | 5 | 5 |
| | 12.5 | 3 | 3 | 5 | 5 |
| 85 | 25 | 5 | 5 | 5 | 5 |
| | 12.5 | 4 | 4 | 5 | 4.5 |
| 86 | 25 | 3 | 4 | 5 | 5 |
| | 12.5 | 2 | 3 | 5 | 3 |
| 88 | 25 | 5 | 5 | 5 | 5 |
| | 12.5 | 5 | 5 | 5 | 5 |
| 89 | 25 | 5 | 5 | 5 | 5 |
| | 12.5 | 5 | 5 | 5 | 5 |
| 90 | 25 | 5 | 5 | 5 | 5 |
| | 12.5 | 4.5 | 5 | 5 | 5 |
| 91 | 25 | 5 | 5 | 5 | 5 |
| | 12.5 | 5 | 5 | 5 | 5 |
| 92 | 25 | 5 | 5 | 5 | 5 |
| | 12.5 | 5 | 5 | 5 | 5 |
| 93 | 25 | 5 | 5 | 5 | 5 |
| | 12.5 | 4.5 | 5 | 5 | 5 |
| 94 | 25 | 5 | 5 | 5 | 5 |
| | 12.5 | 5 | 5 | 5 | 5 |
| 95 | 25 | 5 | 5 | 5 | 5 |
| | 12.5 | 5 | 5 | 5 | 5 |
| 96 | 25 | 5 | 5 | 5 | 5 |
| | 12.5 | 5 | 5 | 5 | 5 |
| 97 | 25 | 5 | 5 | 5 | 5 |
| | 12.5 | 5 | 5 | 5 | 5 |
| 98 | 25 | 5 | 5 | 5 | 5 |
| | 12.5 | 5 | 5 | 5 | 5 |
| 99 | 25 | 5 | 5 | 5 | 5 |
| | 12.5 | 5 | 5 | 5 | 5 |
| 100 | 25 | 5 | 5 | 5 | 5 |
| | 12.5 | 5 | 5 | 5 | 5 |
| 101 | 25 | 5 | 5 | 5 | 5 |
| | 12.5 | 5 | 5 | 5 | 5 |
| 102 | 25 | 5 | 5 | 5 | 5 |
| | 12.5 | 5 | 5 | 5 | 5 |
| 103 | 25 | 5 | 5 | 5 | 5 |
| | 12.5 | 5 | 5 | 5 | 5 |
| 104 | 25 | 5 | 5 | 5 | 5 |
| | 12.5 | 5 | 5 | 5 | 5 |
| 106 | 25 | 5 | 5 | 5 | 5 |
| | 12.5 | 5 | 5 | 5 | 5 |
| 109 | 25 | 4.8 | 5 | 5 | 5 |
| | 12.5 | 2 | 4.5 | 5 | 5 |
| 111 | 25 | 3 | 4.5 | 5 | 5 |
| | 12.5 | 2.5 | 4 | 5 | 5 |
| 113 | 25 | 4 | 5 | 5 | 4.5 |
| | 12.5 | 4 | 4.8 | 5 | 3 |
| 114 | 25 | 5 | 5 | 5 | 5 |
| | 12.5 | 5 | 5 | 5 | 5 |
| 115 | 25 | 4.8 | 4.8 | 5 | 5 |
| | 12.5 | 4.5 | 4.5 | 5 | 4.8 |
| 116 | 25 | 5 | 5 | 5 | 4.8 |
| | 12.5 | 4.8 | 4.8 | 5 | 4.8 |
| 128 | 25 | 5 | 4 | 5 | 5 |
| | 12.5 | 5 | 3 | 5 | 5 |
| 131 | 25 | 5 | 4.5 | 5 | 5 |
| | 12.5 | 5 | 4 | 5 | 5 |
| 134 | 25 | 5 | 4.5 | 5 | 5 |
| | 12.5 | 5 | 4 | 5 | 5 |
| 138 | 25 | 5 | 4 | 5 | 5 |
| | 12.5 | 5 | 3.5 | 5 | 5 |
| 147 | 25 | 5 | 4 | 5 | 5 |
| | 12.5 | 5 | 3.5 | 5 | 3 |
| 148 | 25 | 5 | 4 | 5 | 5 |
| | 12.5 | 5 | 3 | 5 | 3 |
| 149 | 25 | 5 | 5 | 5 | 5 |
| | 12.5 | 5 | 4.5 | 5 | 5 |

| Compound No. | Dosage g/a | Herbicidal effect per-emergence treatment | | | |
|---|---|---|---|---|---|
| | | crabgrass | foxtail | pigweed | lamb's-quarters |
| 160 | 25 | 5 | 4.5 | 5 | 4 |
| | 12.5 | 5 | 4 | 5 | 3.5 |
| 162 | 25 | 5 | 5 | 5 | 5 |
| | 12.5 | 5 | 5 | 5 | 5 |
| 175 | 25 | 4.5 | 3.5 | 5 | 3 |
| | 12.5 | 4 | 3 | 5 | 2.5 |
| Known compound No. 2 | 25 | 5 | 3 | 5 | 4 |
| | 12.5 | 5 | 1 | 1 | 1 |
| Known compound No. 1 | 50 | 0 | 0 | 0 | 0 |
| | 25 | 0 | 0 | 0 | 0 |
| Standard | 25 | 2 | 4 | 3 | 2 |

TABLE 6-continued

| Test Example 4: Pre-emergence soil surface treatment | | | | | |
|---|---|---|---|---|---|
| compound B | 12.5 | 1 | 2 | 1 | 0 |

Remarks:

Standard compound B: 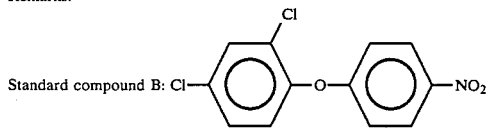

Test Example 5: Post-emergence treatment

A fixed amount of field soil was filled in a round plastic case 8 cm across and 8 cm deep, and a fixed amount of seeds of foxtail, pigweed was sown. When they grew up to 3 to 4-leaf stage, a wettable powder containing the compound of the present invention was sprayed on the body of plants after diluting it at a rate of 12.5, 25 or 50 g of active ingredient per are.

The test was conducted on 2-replication system. Twenty days after the treatment the test results were observed on the same judging standard and the results are shown in Table 7.

TABLE 7

| Test Example 5: Post-emergence treatment | | | |
|---|---|---|---|
| Compound No. | Dosage g/a | Herbicidal effect foxtail | pigweed |
| 1 | 50 | 3 | 5 |
|  | 25 | 2 | 4.5 |
|  | 12.5 | 1 | 4 |
| 3 | 50 | 3 | 5 |
|  | 25 | 2.5 | 5 |
|  | 12.5 | 2 | 4.5 |
| 5 | 50 | 3 | 5 |
|  | 25 | 2.5 | 5 |
|  | 12.5 | 2 | 4.5 |
| 7 | 50 | 5 | 5 |
|  | 25 | 3.5 | 5 |
|  | 12.5 | 3 | 5 |
| 10 | 50 | 4.5 | 5 |
|  | 25 | 4 | 5 |
|  | 12.5 | 3.5 | 5 |
| 11 | 50 | 4 | 5 |
|  | 25 | 3 | 5 |
|  | 12.5 | 2.5 | 5 |
| 12 | 50 | 4 | 5 |
|  | 25 | 3.5 | 5 |
|  | 12.5 | 3 | 5 |
| 13 | 50 | 3.5 | 5 |
|  | 25 | 3 | 5 |
|  | 12.5 | 2 | 4 |
| 14 | 50 | 3 | 5 |
|  | 25 | 2 | 5 |
|  | 12.5 | 1 | 3.5 |
| 21 | 50 | 3 | 5 |
|  | 25 | 2.5 | 4 |
|  | 12.5 | 2 | 3 |
| 27 | 50 | 5 | 5 |
|  | 25 | 5 | 5 |
|  | 12.5 | 3.5 | 5 |
| 28 | 50 | 5 | 5 |
|  | 25 | 5 | 5 |
|  | 12.5 | 4 | 5 |
| 29 | 50 | 4.5 | 5 |
|  | 25 | 3 | 5 |
|  | 12.5 | 2 | 5 |
| 30 | 50 | 4.5 | 5 |
|  | 25 | 3 | 5 |
|  | 12.5 | 2 | 5 |
| 31 | 50 | 3 | 5 |
|  | 25 | 2.5 | 5 |
|  | 12.5 | 2 | 5 |
| 32 | 50 | 4 | 5 |
|  | 25 | 3 | 5 |
| 34 | 12.5 | 2 | 5 |
|  | 50 | 4 | 5 |
|  | 25 | 2.5 | 5 |
| 35 | 12.5 | 2 | 5 |
|  | 50 | 3 | 5 |
|  | 25 | 2.5 | 5 |
| 36 | 12.5 | 2 | 5 |
|  | 50 | 4 | 5 |
|  | 25 | 3 | 5 |
| 37 | 12.5 | 2 | 5 |
|  | 50 | 3.5 | 5 |
|  | 25 | 2.5 | 4 |
| 40 | 12.5 | 2 | 3 |
|  | 50 | 3 | 5 |
|  | 25 | 2.5 | 4.5 |
| 41 | 12.5 | 2 | 3 |
|  | 50 | 3 | 5 |
|  | 25 | 2.5 | 5 |
| 42 | 12.5 | 2 | 4.5 |
|  | 50 | 3.5 | 5 |
|  | 25 | 2.5 | 5 |
| 57 | 12.5 | 2 | 5 |
|  | 50 | 3 | 5 |
|  | 25 | 2 | 5 |
| 60 | 12.5 | 2 | 5 |
|  | 50 | 4 | 5 |
|  | 25 | 3 | 4.5 |
| 63 | 12.5 | 2 | 3 |
|  | 50 | 5 | 5 |
|  | 25 | 5 | 5 |
| 64 | 12.5 | 4.5 | 5 |
|  | 50 | 5 | 5 |
|  | 25 | 5 | 5 |
| 65 | 12.5 | 5 | 5 |
|  | 50 | 5 | 5 |
|  | 25 | 5 | 5 |
| 66 | 12.5 | 5 | 5 |
|  | 50 | 4 | 5 |
|  | 25 | 3.5 | 4 |
| 70 | 12.5 | 2.5 | 3 |
|  | 50 | 3 | 5 |
|  | 25 | 3 | 4.5 |
| 71 | 12.5 | 2 | 3.5 |
|  | 50 | 3 | 5 |
|  | 25 | 2 | 4.5 |
| 72 | 12.5 | 2 | 4 |
|  | 50 | 3 | 5 |
|  | 25 | 2 | 4.5 |
| 81 | 12.5 | 2 | 3 |
|  | 50 | 4 | 5 |
|  | 25 | 3 | 4 |
| 84 | 12.5 | 2 | 4 |
|  | 50 | 4.5 | 5 |
|  | 25 | 4 | 5 |
| 85 | 12.5 | 3 | 5 |
|  | 50 | 4 | 5 |
|  | 25 | 3 | 5 |
| 86 | 12.5 | 2 | 5 |
|  | 50 | 4 | 5 |
|  | 25 | 3 | 5 |
| 87 | 12.5 | 2 | 5 |
|  | 50 | 4 | 5 |
|  | 25 | 3 | 5 |
| 89 | 12.5 | 2 | 5 |
|  | 50 | 5 | 5 |
|  | 25 | 5 | 5 |
| 90 | 12.5 | 5 | 5 |
|  | 50 | 5 | 5 |
|  | 25 | 5 | 5 |
| 91 | 12.5 | 5 | 5 |
|  | 50 | 5 | 5 |
|  | 25 | 5 | 5 |
| 92 | 12.5 | 5 | 5 |
|  | 50 | 5 | 5 |
|  | 25 | 5 | 5 |
| 93 | 12.5 | 5 | 5 |
|  | 50 | 5 | 5 |

TABLE 7-continued

Test Example 5:
Post-emergence treatment

| Compound No. | Dosage g/a | Herbicidal effect foxtail | pigweed |
|---|---|---|---|
| | 25 | 5 | 5 |
| | 12.5 | 5 | 5 |
| 94 | 50 | 5 | 5 |
| | 25 | 5 | 5 |
| | 12.5 | 4.5 | 5 |
| 95 | 50 | 5 | 5 |
| | 25 | 5 | 5 |
| | 12.5 | 4 | 5 |
| 96 | 50 | 5 | 5 |
| | 25 | 5 | 5 |
| | 12.5 | 5 | 5 |
| 97 | 50 | 5 | 5 |
| | 25 | 5 | 5 |
| | 12.5 | 5 | 5 |
| 98 | 50 | 5 | 5 |
| | 25 | 4.5 | 5 |
| | 12.5 | 4 | 5 |
| 99 | 50 | 5 | 5 |
| | 25 | 4.5 | 5 |
| | 12.5 | 3.5 | 5 |
| 100 | 50 | 5 | 5 |
| | 25 | 4.5 | 5 |
| | 12.5 | 4 | 5 |
| 101 | 50 | 5 | 5 |
| | 25 | 4.5 | 5 |
| | 12.5 | 4 | 5 |
| 102 | 50 | 5 | 5 |
| | 25 | 5 | 5 |
| | 12.5 | 4.5 | 5 |
| 103 | 50 | 5 | 5 |
| | 25 | 5 | 5 |
| | 12.5 | 5 | 5 |
| 104 | 50 | 5 | 5 |
| | 25 | 5 | 5 |
| | 12.5 | 5 | 5 |
| 106 | 50 | 5 | 5 |
| | 25 | 5 | 5 |
| | 12.5 | 5 | 5 |
| 146 | 50 | 3 | 5 |
| | 25 | 2 | 5 |
| | 12.5 | 1 | 5 |
| 150 | 50 | 5 | 5 |
| | 25 | 5 | 5 |
| | 12.5 | 3 | 5 |
| 151 | 50 | 5 | 5 |
| | 25 | 5 | 5 |
| | 12.5 | 3 | 5 |
| 162 | 50 | 5 | 5 |
| | 25 | 5 | 5 |
| | 12.5 | 5 | 5 |
| 177 | 50 | 4 | 5 |
| | 25 | 3.5 | 5 |
| | 12.5 | 3 | 5 |
| 178 | 50 | 2 | 5 |
| | 25 | 1 | 4.5 |
| | 12.5 | 0.5 | 3.5 |
| Known compound No. 1 | 50 | 0 | 0.5 |
| | 25 | 0 | 0 |
| | 12.5 | 0 | 0 |
| Known compound No. 2 | 50 | 0 | 4 |
| | 25 | 0 | 0.5 |
| | 12.5 | 0 | 0 |
| standard compound B | 50 | 2.5 | 4 |
| | 25 | 2 | 3 |
| | 12.5 | 0 | 1 |

Test Example 6: Phytotoxicity against crops

A fixed amount of field soil was filled in a plastic vessel sized 23 cm×4.5 cm×12.5 cm and a fixed amount of seeds of soybean, cotton, corn, wheat, sunflower and rice was sown followed by 3-cm thick covering with soil.

Then immediately a diluted solution of the compound of the present invention was sprayed on the soil surface with a small sprayer at the rate of 25 to 50 g of the compound of the present invention.

After the treatment the crops were grown in a greenhouse and 20 days later the degree of phytoloxicity against each crop was observed. The test was carried out on 2-replication system and each average value was sought.

The judging standard of test results is the same with Test Example 1 and the result are shown in Table 8.

TABLE 8

Test Example 6

| Compound No. | Dosage g/a | Phytotoxicity against crops soybean | cotton | corn | wheat | rice | sunflower |
|---|---|---|---|---|---|---|---|
| 2 | 50 | — | — | — | — | — | — |
| | 25 | — | — | — | — | — | — |
| 3 | 50 | ± | — | — | — | — | — |
| | 25 | — | — | — | — | — | — |
| 5 | 50 | — | — | — | — | — | — |
| | 25 | — | — | — | — | — | — |
| 6 | 50 | — | — | — | — | — | — |
| | 25 | — | — | — | — | — | — |
| 7 | 50 | ± | — | ± | ± | — | — |
| | 25 | — | — | — | — | — | — |
| 8 | 50 | — | — | — | — | — | — |
| | 25 | — | — | — | — | — | — |
| 9 | 50 | — | — | — | — | — | — |
| | 25 | — | — | — | — | — | — |
| 10 | 50 | ± | — | — | — | — | — |
| | 25 | — | — | — | — | — | — |
| 11 | 50 | — | — | — | — | — | — |
| | 25 | — | — | — | — | — | — |
| 13 | 50 | — | — | — | — | — | — |
| | 25 | — | — | — | — | — | — |
| 14 | 50 | — | — | — | — | — | — |
| | 25 | — | — | — | — | — | — |
| 18 | 50 | — | — | — | — | — | — |
| | 25 | — | — | — | — | — | — |
| 27 | 50 | ± | — | ± | ± | — | — |
| | 25 | — | — | — | — | — | — |
| 28 | 50 | — | — | — | — | — | — |
| | 25 | — | — | — | — | — | — |
| 29 | 50 | — | — | — | — | — | — |
| | 25 | — | — | — | — | — | — |
| 30 | 50 | ± | — | — | — | — | — |
| | 25 | — | — | — | — | — | — |
| 31 | 50 | ± | — | — | — | — | — |
| | 25 | — | — | — | — | — | — |
| 33 | 50 | — | — | — | — | — | — |
| | 25 | — | — | — | — | — | — |
| 34 | 50 | ± | — | — | — | — | — |
| | 25 | — | — | — | — | — | — |
| 40 | 50 | — | — | — | — | — | — |
| | 25 | — | — | — | — | — | — |
| 41 | 50 | — | — | ± | ± | — | — |
| | 25 | — | — | — | — | — | — |
| 42 | 50 | ± | — | ± | ± | — | — |
| | 25 | — | — | — | — | — | — |
| 43 | 50 | — | — | — | — | — | — |
| | 25 | — | — | — | — | — | — |
| 44 | 50 | — | — | — | — | — | — |
| | 25 | — | — | — | — | — | — |
| 48 | 50 | — | — | — | — | — | — |
| | 25 | — | — | — | — | — | — |
| 49 | 50 | — | — | — | — | — | — |
| | 25 | — | — | — | — | — | — |
| 63 | 50 | — | — | ± | ± | — | — |
| | 25 | — | — | — | — | — | — |
| 64 | 50 | — | — | — | — | — | — |
| | 25 | — | — | — | — | — | — |
| 65 | 50 | — | — | — | — | — | — |
| | 25 | — | — | — | — | — | — |
| 74 | 50 | — | — | — | — | — | — |
| | 25 | — | — | — | — | — | — |
| 80 | 50 | — | — | — | — | — | — |
| | 25 | — | — | — | — | — | — |
| 83 | 50 | — | — | ± | ± | — | — |
| | 25 | — | — | — | — | — | — |
| 84 | 50 | ± | — | — | — | — | — |
| | 25 | — | — | — | — | — | — |

TABLE 8-continued

| Compound No. | Dosage g/a | Test Example 6 Phytotoxicity against crops | | | | | |
|---|---|---|---|---|---|---|---|
| | | soybean | cotton | corn | wheat | rice | sunflower |
| 85 | 50 | ± | − | ± | ± | − | − |
| | 25 | − | − | − | − | − | − |
| 86 | 50 | ± | − | − | − | − | − |
| | 25 | − | − | − | − | − | − |
| 88 | 50 | − | − | − | − | − | − |
| | 25 | − | − | − | − | − | − |
| 90 | 50 | − | − | ± | + | ± | − |
| | 25 | − | − | − | ± | ± | − |
| 91 | 50 | − | − | ± | ± | ± | − |
| | 25 | − | − | − | − | ± | − |
| 92 | 50 | − | − | ± | − | ± | − |
| | 25 | − | − | − | − | − | − |
| 93 | 50 | − | − | ± | − | ± | − |
| | 25 | − | − | ± | − | − | − |
| 94 | 50 | − | − | ± | + | ± | − |
| | 25 | − | − | ± | − | − | − |
| 95 | 50 | − | − | + | + | ± | − |
| | 25 | − | − | − | − | − | − |
| 96 | 50 | − | − | ± | ± | ± | − |
| | 25 | − | − | − | ± | ± | − |
| 97 | 50 | − | − | ± | ± | ± | − |
| | 25 | − | − | − | ± | − | − |
| 98 | 50 | − | − | ± | − | ± | − |
| | 25 | − | − | − | − | − | − |
| 99 | 50 | − | − | − | ± | − | − |
| | 25 | − | − | − | − | − | − |
| 100 | 50 | − | − | ± | ± | ± | − |
| | 25 | − | − | − | − | − | − |
| 101 | 50 | − | − | ± | ± | ± | − |
| | 25 | − | − | − | ± | − | − |
| 102 | 50 | − | − | ± | ± | ± | − |
| | 25 | − | − | − | ± | − | − |
| 103 | 50 | − | − | ± | − | − | − |
| | 25 | − | − | − | − | − | − |
| 104 | 50 | − | − | ± | − | − | − |
| | 25 | − | − | − | − | − | − |
| 105 | 50 | − | − | ± | ± | ± | − |
| | 25 | − | − | − | ± | − | − |
| 106 | 50 | − | − | − | − | − | − |
| | 25 | − | − | − | − | − | − |
| 107 | 50 | − | − | − | − | − | − |
| | 25 | − | − | − | − | − | − |
| 130 | 50 | − | − | − | − | − | − |
| | 25 | − | − | − | − | − | − |
| 131 | 50 | − | − | − | − | − | − |
| | 25 | − | − | − | − | − | − |
| 148 | 50 | − | − | − | − | − | − |
| | 25 | − | − | − | − | − | − |
| 149 | 50 | ± | − | − | − | − | − |
| | 25 | − | − | − | − | − | − |
| 150 | 50 | − | − | − | − | − | − |
| | 25 | − | − | − | − | − | − |
| 162 | 50 | − | − | − | − | − | − |
| | 25 | − | − | − | − | − | − |
| 177 | 50 | − | − | − | − | − | − |
| | 25 | − | − | − | − | − | − |
| Known compound No. 1 | 50 | − | − | − | − | − | − |
| | 25 | − | − | − | − | − | − |
| Known compound No. 2 | 50 | − | − | − | − | − | − |
| | 25 | − | − | − | − | − | − |
| Standard compound B | 50 | +++ | ++ | ++ | +++ | ++ | +++ |
| | 25 | ++ | + | + | ++ | + | ++ |

As obvious from the results of Test Examples 4 and 5, the compound of the present invention proves to show very good herbicidal activity both in pre-emergence and post-emergence treatments of main weeds in the field. On the other hand, it is clear from the results of Test Example 6 that the compound of the present invention has no phytotoxicity against crops and is a suitable herbicide for use in farmlands.

What is claimed is:

1. An N-substituted-$\Delta^1$-tetrahydrophthalimide derivative represented by the formula:

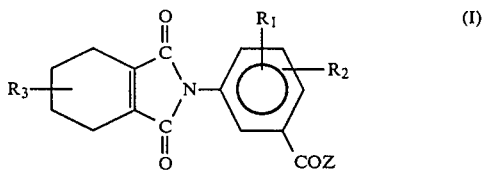

wherein $R_1$ is hydrogen, halogen, lower alkyl, lower alkoxy or nitro, $R_2$ is hydrogen, lower alkyl or halogen, $R_3$ is hydrogen or lower alkyl and Z is hydroxy, straight or branched chain $C_1$–$C_8$ alkoxy that may have halogen, lower alkoxy, lower alkoxyalkyl or cyano as substitution groups, $C_3$–$C_7$ alicyclic alkoxy, $C_2$–$C_5$ alkenyloxy, $C_3$–$C_4$ alkynyloxy, phenoxy that may have halogen, lower alkyl or lower alkoxy as substitution groups, benzyl- or phenethyloxy that may have halogen, lower alkyl or lower alkoxy as substitution groups, $C_1$–$C_8$ alkylthio, amino, primary or secondary $C_1$–$C_8$ alkylamino that may have halogen or hydroxy as substitution groups, $C_3$–$C_5$ alkenylamino that may have halogen as substitution groups, morpholino that may have lower alkyl as substitution groups or metal salt of hydroxy provided that when $R_1$, $R_2$ and $R_3$ are hydrogen, Z is not hydroxy.

2. An N-substituted-$\Delta^1$-tetrahydrophthalimide derivative according to claim 1 wherein $R_1$ is halogen or lower alkyl, $R_2$ is hydrogen, lower alkyl or halogen, $R_3$ is hydrogen or lower alkyl and Z is hydroxy, alkoxy having 1 to 8 carbon atoms that may have halogen or lower alkoxy, lower alkoxyalkoxy or cyano as substitution groups, alicyclic alkoxy having 3 to 7 carbon atoms, alkenyloxy having 2 to 5 carbon atoms or alkyl thio having 1 to 8 carbon atoms, primary or secondary alkylamino having 1 to 8 carbon atoms that may have halogen or hydroxy as substitution groups of alkenylamino having 3 to 5 carbon atoms that may have halogen group, or metal salt of hydroxy.

3. An N-substituted-$\Delta^1$-tetrahydrophthalimide derivative according to claim 1 wherein $R_1$ is halogen or lower alkyl, $R_2$ is hydrogen, lower alkyl or halogen, $R_3$ is hydrogen or lower alkyl and Z is alkoxy having 1 to 8 carbon atoms that may have lower alkoxy or cyano as substitution groups, primary alkylamino having 1 to 8 carbon atoms that may have halogen and hydroxy as substitution groups, metal salt of hydroxy or hydroxy.

4. An N-substituted-$\Delta^1$-tetrahydrophthalimide derivative according to claim 1 wherein $R_1$ is Cl or Br, $R_2$ is hydrogen, Cl, Br or F, $R_3$ is hydrogen or methyl and Z is alkoxy having 2 to 4 carbon atoms.

5. The compound of claim 4 which is N-(4,6-dichloro-3-isopropoxycarbonylphenyl) $\Delta^1$-tetrahydrophthalimide.

6. The compound of claim 4 which is N-(4,6-dichloro-3-sec-butoxycarbonylphenyl)-$\Delta^1$-tetrahydrophthalimide.

7. The compound of claim 4 which is N-(4-bromo-3-isopropoxycarbonylphenyl)-$\Delta^1$-tetrahydrophthalimide.

8. The compound of claim 4 which is N-(4-chloro-6-fluoro-3-ethoxycarbonylphenyl)-$\Delta^1$-tetrahydrophthalimide.

9. The compound of claim 4 which is

N-(4-chloro-6-fluoro-3-isopropoxycarbonylphenyl)-Δ¹-tetrahydrophthalimide.

10. The compound of claim 4 which is N-(4-chloro-6-fluoro-3-sec-butoxycarbonylphenyl)-Δ¹-tetrahydrophthalimide.

11. The compound of claim 4 which is N-(4-bromo-6-fluoro-3-isopropoxycarbonylphenyl)-Δ¹-tetrahydrophthalimide.

12. The compound of claim 4 which is N-(4-bromo-6-fluoro-3-ethoxycarbonylphenyl)-Δ¹-tetrahydrophthalimide.

13. The compound of claim 4 which is N-(4-bromo-6-fluoro-3-sec-butoxycarbonylphenyl)-Δ¹-tetrahydrophthalimide.

14. The compound of claim 4 which is N-(4-chloro-6-fluoro-3-isopropoxycarbonylphenyl)-4-methyl-Δ¹-tetrahydrophthalimide.

15. The compound of claim 4 which is N-(4,6-dichloro-3-ethoxycarbonylphenyl)-Δ¹-tetrahydrophthalimide.

16. The compound of claim 4 which is N-(4-chloro-3-isopropoxycarbonylphenyl)-Δ¹-tetrahydrophthalimide.

17. The compound of claim 4 which is N-(4-chloro-3-sec-butoxycarbonylphenyl)-Δ¹-tetrahydrophthalimide.

18. N-(4-chloro-6-fluoro-3-sec-butoxycarbonylphenyl)-4-methyl-Δ¹-tetrahydrophthimide.

19. N-(4-chloro-3-n-propoxycarbonylphenyl)-Δ¹-terahydrophthalimide.

20. N-(4-bromo-6-fluoro-isopropoxycarbonylphenyl)-4-methyl-Δ¹-tetrahydrophthalimide.

21. A herbicidal composition comprising 0.1 to 95% by weight of a new N-substituted-Δ¹-tetrahydrophthalimide derivative represented by the formula:

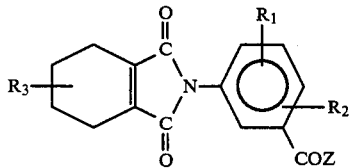

wherein $R_1$ is hydrogen, halogen, lower alkyl, lower alkoxy or nitro, $R_2$ is hydrogen, lower alkyl or halogen, $R_3$ is hydrogen or lower alkyl and Z is hydroxy, straight or branched chain $C_1$-$C_8$ alkoxy that may have halogen, lower alkoxy, lower alkoxyalkoxy or cyano as substitution groups, alicyclic alkoxy, alkenyloxy, alkynyloxy, phenoxy that may have halogen, lower alkyl or lower alkoxy as substitution groups, aralkyloxy that may have halogen, lower alkyl or lower alkoxy as substitution groups, alkylthio, amino, primary or secondary alkylamino that may have halogen and hydroxy as substitution groups, alkenylamino that may have halogen as substitution groups, morpholino that may have lower alkyl as substitution groups or metal salt of hydroxy provided that when $R_1$, $R_2$ and $R_3$ are hydrogen, Z is not hydroxyl and 5 to 99.9% by weight of adjuvants.

22. A herbicidal composition according to claim 21 comprising the N-substituted-Δ¹-tetrahydrophthalimide derivative as an active ingredient, represented by the formula (I) wherein $R_1$ is halogen or lower alkyl, $R_2$ is hydrogen, lower alkyl or halogen, $R_3$ is hydrogen or lower alkyl and Z is hydroxy, alkoxy having 1 to 8 carbon atoms that may have halogen, lower alkoxy or cyano, alicyclic alkoxy having 3 to 7 carbon atoms, alkenyloxy having 2 to 5 carbon atoms or alkylthio having 1 to 8 carbon atoms, primary or secondary alkylamino having 1 to 8 carbon atoms that may have halogen or hydroxy as substitution groups or alkenylamino having 3 to 5 carbon atoms that may have halogen group or metal salt of hydroxy.

23. The herbicidal composition according to claim 21 comprising the N-substituted-Δ¹-tetrahydrophthalimide derivative as an active ingredient, wherein $R_1$ is halogen or lower alkyl, $R_2$ is hydrogen, lower alkyl or halogen, $R_3$ is hydrogen or lower alkyl and Z is alkoxy having 1 to 8 carbon atoms that may have lower alkoxy as substitution groups, primary alkylamino having 1 to 8 carbon atoms that may have halogen and hydroxy as substitution groups, metal salt of hydroxy or hydroxy.

24. The herbicidal composition according to claim 21 comprising the N-substituted-Δ¹-tetrahydrophthalimide derivative as an active ingredient, wherein $R_1$ is Cl or Br, $R_2$ is hydrogen, Cl, Br or F, $R_3$ is hydrogen or methyl and Z is chain alkoxy having 2 to 4 carbon atoms.

25. A method for killing weeds which comprises applying to weeds or the locus thereof a herbicidally effective amount of N-substituted-Δ¹-tetrahydrophthalimide derivatives of formula:

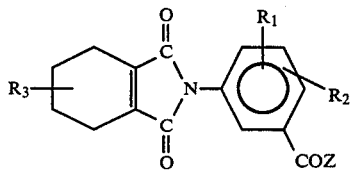

wherein $R_1$ is hydrogen, halogen, lower alkyl, lower alkoxy or nitro, $R_2$ is hydrogen, lower alkyl or halogen, $R_3$ is hydrogen or lower alkyl and Z is hydroxy, straight or branched chain $C_1$-$C_8$ alkoxy that may have halogen, lower alkoxy, lower alkoxyalkoxy or cyano as substitution groups, alicyclic alkoxy, alkenyloxy, alkynyloxy, phenoxy that may have halogen, lower alkyl or lower alkoxy as substitution groups, aralkyloxy that may have halogen, lower alkyl or lower alkoxy as substitution groups, alkylthio, amino, primary or secondary alkylamino that may have halogen or hydroxyl groups as substitution groups, alkenylamino that may have halogen as substitution groups, morpholino that may have lower alkyl as substitution groups or metal salt of hydroxy provided that when $R_1$, $R_2$ and $R_3$ are hydrogen, Z is not hydroxy.

26. The method according to claim 25 wherein $R_1$ is halogen or lower alkyl, $R_2$ is hydrogen, lower alkyl or halogen, $R_3$ is hydrogen or lower alkyl and Z is hydroxy, chain alkoxy having 1 to 8 carbon atoms that may have halogen, lower alkoxy or cyano as substitution groups, alicyclic alkoxy having 3 to 7 carbon atoms, alkenyloxy having 2 to 5 carbon atoms or alkylthio having 1 to 8 carbon atoms, primary or secondary alkylamino having 1 to 8 carbon atoms that may have halogen or hydroxy, or alkenylamino having 3 to 5 carbon atoms or metal salt of hydroxy.

27. The method of claim 25 wherein $R_1$ is halogen or lower alkyl, $R_2$ is hydrogen, lower alkyl or halogen, $R_3$ is hydrogen or lower alkyl and Z is alkoxy having 1 to 8 carbon atoms that may have lower alkoxy or cyano as substitution groups primary alkylamino having 1 to 8 carbon atoms that may have halogen and hydroxy as substitution groups, metal salt of hydroxy or hydroxy.

28. The method of claim 25 wherein $R_1$ is Cl or Br, $R_2$ is hydrogen, Cl, Br or F, $R_3$ is hydrogen or $CH_3$, Z is alkoxy having 2–4 carbon atoms.

* * * * *